United States Patent [19]

Bernstein et al.

[11] Patent Number: 5,758,033
[45] Date of Patent: May 26, 1998

[54] AUTOMATED TISSUE ASSAY USING STANDARDIZED CHEMICALS AND PACKAGES

[75] Inventors: Steven A. Bernstein, Los Olivos; Page A. Erickson; Stephen Barker, both of Santa Barbara, all of Calif.

[73] Assignee: Biotek Solutions, Incorporated, Santa Barbara, Calif.

[21] Appl. No.: 668,377

[22] Filed: Jun. 21, 1996

Related U.S. Application Data

[60] Division of Ser. No. 252,282, May 31, 1994, Pat. No. 5,696,887, which is a continuation-in-part of Ser. No. 740,285, Aug. 5, 1991, Pat. No. 5,355,439, and Ser. No. 218,143, Mar. 24, 1994, Pat. No. 5,675,715.

[51] Int. Cl.⁶ .............................. G06F 9/00; G06F 15/46
[52] U.S. Cl. ........................................ 395/80; 395/82
[58] Field of Search .................................. 395/80, 82

[56] References Cited

U.S. PATENT DOCUMENTS

| | | | |
|---|---|---|---|
| 4,835,711 | 5/1989 | Hutchins et al. | 395/82 |
| 4,869,813 | 9/1989 | Baily et al. | 901/47 |
| 5,593,293 | 1/1997 | Machino et al. | 414/729 |

*Primary Examiner*—George B. Davis
*Attorney, Agent, or Firm*—McDonnell Boehnen Hulbert & Berghoff

[57] ABSTRACT

A system which performs a plurality of independent analysis procedures simultaneously, possibly involving differing types of tissues and differing process steps, comprising a robotic arm, which may move the different tissue samples among the plurality of processing stations, and a processor, which may select the order, timing and location of the tissue sample. The robotic device may comprise a bench robot with rectilinear motion or a rotatable tower. The processing stations may be disposed in a set of grid locations, which comprise workstations for performing individual steps of the procedures. In response to timing information about the procedures, the processor may select the sample to be moved. The processor may examine the multiple procedures for timing conflicts and it may adjust the sequence of steps for the procedures, the timing of steps with a specified range of times, or the order of the samples in order to avoid conflicts and to minimize the total time required by the system to complete the procedures. The operator may create or edit templates for workstations, create or edit lists of process steps for procedures, monitor the progress of ongoing procedures, or override the determination of what process steps to perform.

11 Claims, 18 Drawing Sheets

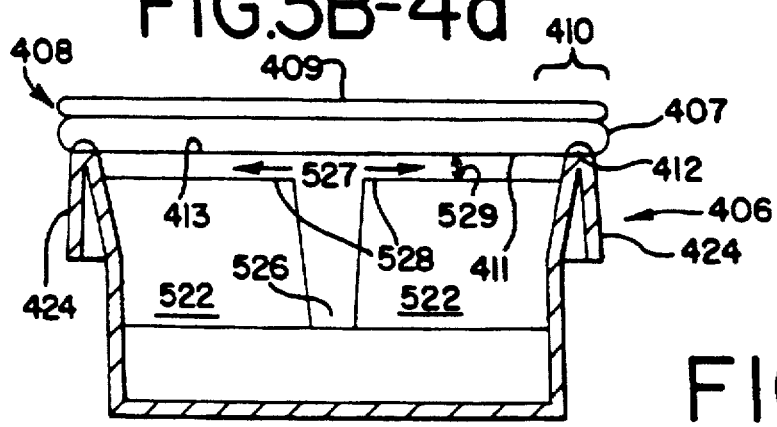
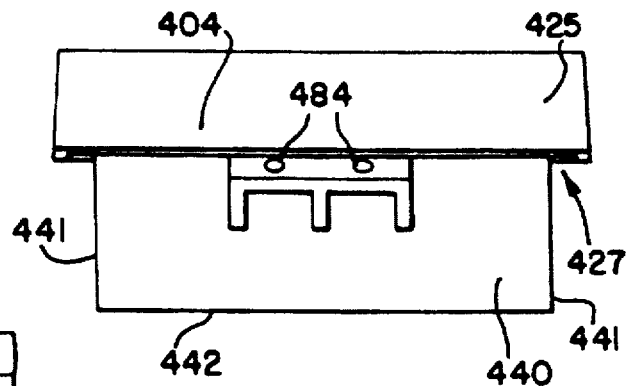
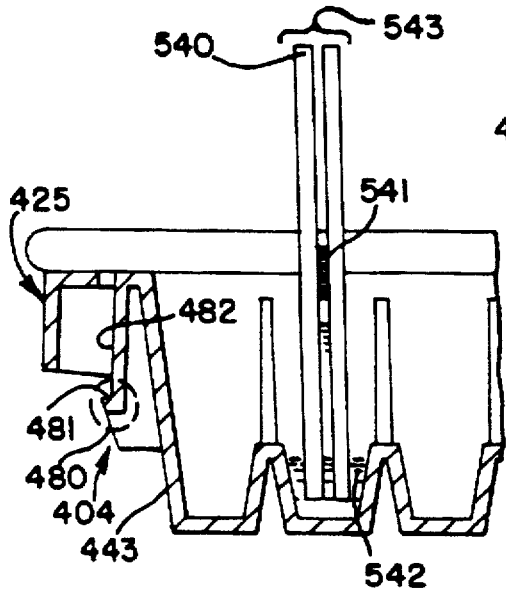
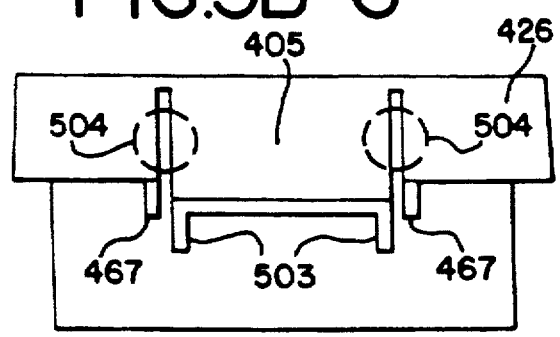
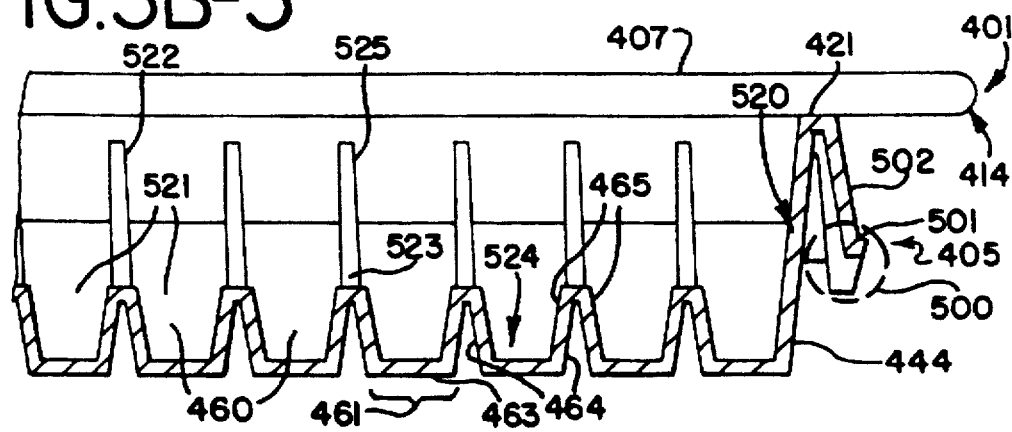

FIG.3C-3d
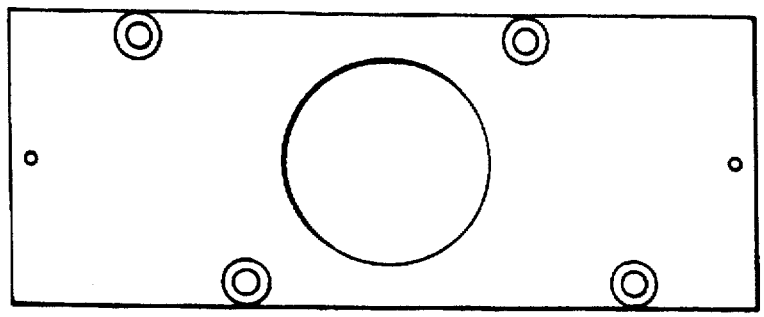
FIG.3C-3e
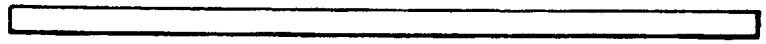
FIG.3C-3f            FIG.3C-3h
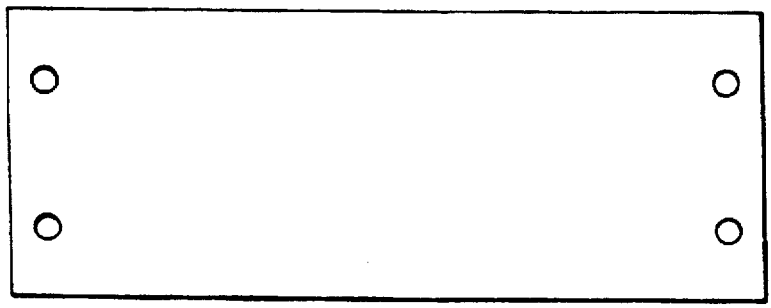 
FIG.3C-3g
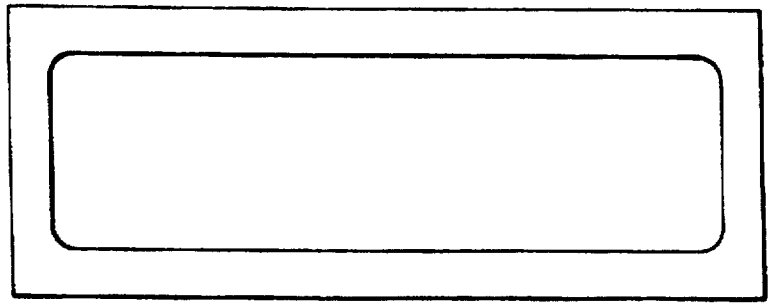

FIG.3C-3i
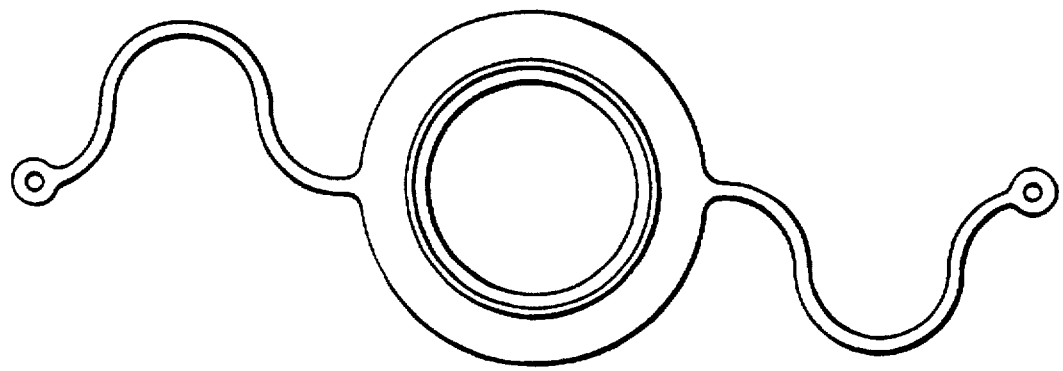
FIG.3C-3k  FIG.3C-3l
FIG.3C-3j
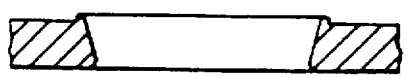
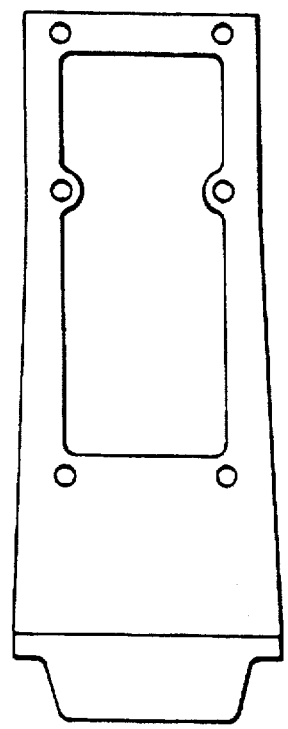
FIG.3C-3m  FIG.3C-3n
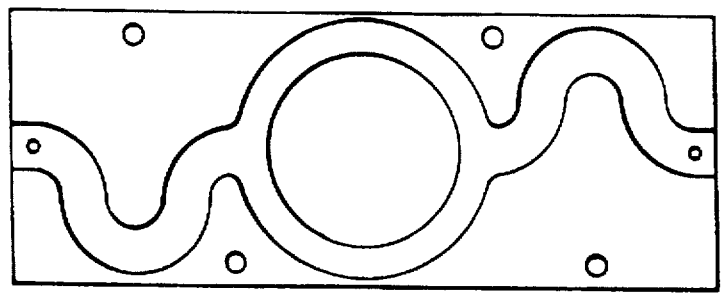

FIG.3C-3u
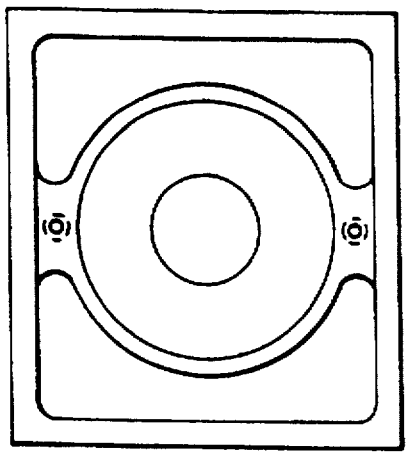
FIG.3C-3v
FIG.3C-3x
FIG.3C-3w
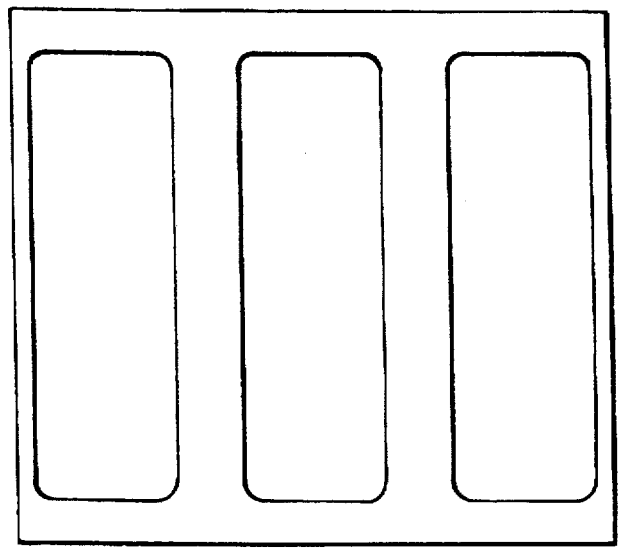
FIG.3C-3z
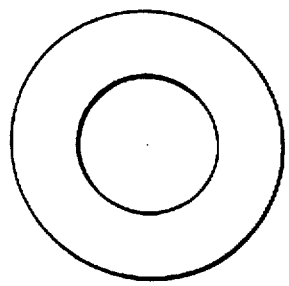
FIG.3C-3y
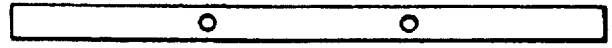

AUTOMATED TISSUE ASSAY USING STANDARDIZED CHEMICALS AND PACKAGES

CROSS-REFERENCE TO RELATED APPLICATION

This application is a divisional of application Ser. No. 08/252,282, filed May 31, 1994, U.S. Pat. No. 5,696,887 which is a continuation-in-part of application Ser. No. 07/740,285 filed Aug. 5, 1991, U.S. Pat. No. 5,355,439 and continuation in part of application Ser. No. 08/218,143, filed Mar. 24, 1994, U.S. Pat. No. 5,675,715.

BACKGROUND OF THE INVENTION

1. Field of the Invention

This invention relates to methods and apparatus useful in automated analysis or testing of tissue samples, and to automated tissue assay using standardized chemicals and packages.

2. Description of Related Art

The analysis of tissue is a valuable diagnostic tool used by the pathologist to diagnose many illnesses and by the medical researcher to obtain information about a cell structure.

In order to obtain information from a tissue sample it is usually necessary to perform a number of preliminary operations to prepare the sample for analysis. There are many variations of the procedures to prepare tissue samples for testing. These variations may be considered refinements to adapt the process for individual tissues or because a particular technique is better suited to identify a specific chemical substance or enzyme within the tissue sample. However the basic preparation techniques are essentially the same.

Typically such operations might include the processing of the tissue by fixation, dehydration, infiltration and embedding; mounting of the tissue on a slide and then staining the sample; labeling of the tissue through the detection of various constituents; grid staining of tissue sections for analysis by an electron microscope or the growing of sample cells in culture dishes.

Depending on the analysis or testing to be done, a sample may have to undergo a number of preliminary steps or treatments or procedures before it is ready to be analyzed for its informational content. Typically the procedures are complex and time consuming, involving many tightly sequenced steps often utilizing expensive and toxic materials.

These procedures must usually be performed in a critical order for each sample and each treatment is frequently time dependent. Additionally the laboratory is often under extreme pressure to perform many different analysis as soon as possible, entailing many different procedures and tests.

A sample of tissue may undergo an optical microscopic examination so that the relationship of various cells to each other may be determined or abnormalities may be uncovered. The tissue sample must be an extremely thin strip of tissue so that light may be transmitted therethrough. The average thickness of the tissue sample or slice (often referred to as sections) is on the order of 2 to 8 microns. A relatively soft and pliable tissue such as might come from an organ of the human body, in its fresh state cannot be accurately cut into such thin sections. In addition, in order to see the individual constituents of the cells, such as the nucleus, the nucleolus, the cytoplasm and the cell membrane, it is preferable to have them colored by different dyes to produce a contrasting appearance between the elements. Very limited dye staining can be done on fresh or recently living tissue without resorting to chemical processing. Typically a sample of tissue 2.0 to 2.5 square centimeters in area and 3 to 4 millimeters thick is utilized. The tissue sample is then fixed in a material (a fixative) which not only preserves the cellular structure but also stops any further enzymic action which could result in the putrification or autolysis of the tissue. While many substances can function as a fixative, a 4% formaldehyde or a 10% formalin solution is very common. Other common fixatives would include ethanol, picric acid or mercuric chloride usually with formalin. It should be remembered that in dealing with these substances the containers holding the materials must be suitable. For example mercuric chloride severely corrodes metals and therefore should normally be contained in a glass vessel.

To prepare good samples for microscopic examination the initial step should kill the enzymic processes of the tissue and should alter or denature the proteins of the cell through fixation. The period of fixation may take several hours or even a few days depending upon the tissue type, sample size and type of fixative being used.

After fixation, the tissue sample is often dehydrated by the removal of water from the sample through the use of increasing strengths of alcohol or of some other dehydrating fluid. Gradual dehydration is preferred because it causes less distortion to the sample than a rapid dehydration process.

The alcohol is then replaced by a chemical which mixes with wax or some other plastic substance which can permeate the tissue sample and give it a consistency suitable for the preparation of thin sections without disintegration or splitting. Fat solvents, such as chloroform or toluene are commonly used for this step. The sample, which has been dehydrated by the infiltration of alcohol, is next exposed to several changes of solvent over a period that may last from a few hours to days until the alcohol is completely replaced by the solvent. The sample is then exposed to a wax which is soluble in the solvent. If a paraffin type wax is used the infiltration is at a temperature above its melting point. After the wax infiltration the sample is allowed to cool and the wax solidify so that the sample is entirely embedded in and infiltrated by the wax.

A microtome is then utilized to cut thin slices from the tissue sample. The slices are on the order of 5 to 6 microns thick. The cut thin sections are floated on water to spread or flatten the section. The section is then disposed on a glass slide, usually measuring about 8 by 2.5 millimeters.

The wax is then removed by exposing the sample to a solvent, the solvent removed by alcohol, and the alcohol removed by decreasing the alcoholic concentrations until eventually the tissue is once more infiltrated by water. The infiltration of the sample by water permits the staining of the cell constituents by water soluble dyes.

Prior to the development of automated procedures for the preparation of tissue samples, it often took from 2 to 10 days before the tissue could be examined under a microscope. In more recent years automated processes have been developed utilizing apparatus to transfer the sample from one fluid to another at defined intervals, and as a result the preparation time has been significantly reduced to between about 4 and 16 hours.

Variations in the materials used in the preparation of the sample are advantageous under some circumstances. The use of ester wax allows sections 1 to 3 microns thick to be cut with less contraction than that which occurs when paraffin used. The sample is exposed to higher temperatures when paraffin wax is used. The use of cellulose nitrate embedding shrinks tissues less than wax, produces good cohesion between tissue layers and permits large undistorted sections to be cut 25 to 30 microns thick, if so desired. It is clear that persons with skill in the art of tissue preparation may use many different materials to which the samples may be exposed.

Tissue staining is a procedure which is utilized to make microscopic structures more visible. Perhaps the most common stain materials are hematoxylin and eosin. Hematoxylin is utilized to clearly stain the nuclei of cells dark blue. Eosin is used to stains the cell cytoplasm various shades of red or yellow, presenting a clear contrast to the blue stain of the nuclei.

Many synthetic dyes are derived from benzene which is colorless but by changing its chemical configuration color compounds are produced which are called chromophores. It is these chromophores which constitute the bulk of the different coloring dyes used in research and routine histology.

There are many techniques by which sample tissues may be stained and most of these techniques require exposing the sample to various solutions. Histochemistry is the science by which chemical reactions are used to identify particular substances in tissues. In addition, many enzymes can be detected by exposing a sample to a particular chemical substance on which the enzyme is known to have an effect such as turning the substance into a colored marker. Thus from the above it can be seen that a sample tissue may be exposed to various antibodies, enzyme labeled detection systems, colormetric substrates, counterstains, washing buffers and organic reagents.

Many experimental and observational research projects involve experimentation to authenticate new techniques and these experiments can be very extensive and time consuming.

In addition to the techniques that prepare samples for optical microscopy, techniques often must be utilized which make the use of electron microscopes suitable in the examination of tissue samples. Actually it has been found that the pathological examination of almost any disorder makes electron microscopy highly desirable and often essential.

Tissue samples for use with an electron microscope may be fixed in glutaraldehyde or osmium tetroxide rather than in the standard fixatives used for optical microscopy samples. Usually very small samples of tissue are embedded in methacrylate or epoxy resin and thin sections are cut (about 0.06 microns thick). Staining is most often done by colored solutions and not dyes, and heavy metal salts are utilized to enhance contrasts of density.

From the above brief description of some of the techniques and materials used by a pathologist in the examination of tissues, it can be seen that for a research laboratory to carry out such a wide variety of processes and numerous different tests assisting apparatus would be desirable and almost mandatory. Other and further information about tissue analysis and tissue assays may be found in the following references, each of which is hereby incorporated by reference as if fully set forth herein:

Bancroft, J. D. and A. Stevens. Theory and Practice of Histological Techniques (3rd ed. 1990). Churchill Livingstone: Edinburgh. ISBN 0-443-03559-8.

Childs, G. W. Immunocytochemical Technology (1986). Alan R. Liss, Inc.: New York. ISBN 0-8451-4213-5.

Culling, C. F. A., R. T. Allison and W. T. Barr. Cellular Pathology Technique (4th ed. 1985). Butterworths: London. ISBN 0-407-72903-8.

Sternberger, L. A. Immunocytochemistry (2nd ed. 1979). John Wiley & Sons: New York. ISBN 0-471-03386-3.

Many pathology laboratories have in fact automated many of the simple and routine procedures described above such as simple staining or sample embedding. Where the same procedure is repeated with great frequency, laboratories have often designed specialized machines to perform the often repeated testing simultaneously on many samples. Typical of such machines are the equipment used in the routine analysis of blood samples. The equipment used in this type of laboratory is capable of treating multiple samples simultaneously to the same testing procedure, i.e., parallel testing or through the use of multiple machines the same result of parallel testing, is achieved. Alternatively the laboratory may perform the same test repetitively, i.e., sequentially and thus subsequent samples may be subject to a significant time delay.

Research laboratories often are required to perform non-routine analysis requiring many different test procedures. As a result of this lack of repetitive procedures, research laboratories have relatively little automated equipment to assist the researchers in their task. The most obvious reason for this lack of automation is that the equipment presently available is dedicated to a limited number of procedures most commonly performed. The equipment is not flexible enough to permit a wide variety of operations to be easily accomplished nor does the present equipment permit easy and facile changes to the operations.

Another problem that has arisen in the art of repeated testing is that of reagent supply. Typically, devices to perform repeated testing must be loaded with bulk reagents, and those bulk reagents must have sufficient volume that a specimen slide can be immersed in the reagent, at least to the level of the specimen. This can be wasteful of expensive reagents. It can also result in substantial contamination with the reagent of the back or sides of the slide, resulting in significant carryover of the reagent and its chemical effect into a next step, and a possible safety hazard for the operator or support personnel.

Another problem that has arisen in the art of repeated testing is that of packaging of reagents for tests. Typically, devices to perform repeated testing comprise isolator pads, essentially hydrophobic surfaces of glass or plastic, with roughened areas to contain the reagent and smooth areas to repel it. This can cause two problems. First, if too much of the reagent is doled out by the operator, it can overflow the isolator pad and mix with another reagent. Second, the reagent has a near maximal surface/volume ratio, often resulting in significant evaporation of the reagent before use.

SUMMARY OF THE INVENTION

The invention provides a system which performs a plurality of independent analysis procedures simultaneously, possibly involving differing types of tissues and differing process steps. The system comprises a robotic arm, which may move the different tissue samples among a plurality of processing stations, and a processor, which may select the next tissue sample to move, when to move it, and where to move it to. In a preferred embodiment, the processor may direct the robotic arm to interleave the differing process steps, for example by time division multiplexing.

In a preferred embodiment, the processing stations may be disposed in a set of grid locations, so that the location of any one processing station may be specified by an X coordinate and a Y coordinate, and possibly a Z coordinate for height. The robotic device may comprise a bench robot with sufficient degrees of freedom that it is able to reach each of the grid locations with suitable movement. The processing stations may comprise workstations for performing individual steps of the tissue assay procedures, such as solution trays, or other equipment useful in bioassay, biomedical or related environments.

In a preferred embodiment, the processor may select a tissue sample to be moved in response to timing information about the procedures, which may specify a time duration range (e.g., a minimum time and maximum time) each process step should take. The processor may determine the exact time for a step by generating a possible sequence of steps and examining that sequence for conflicts, adjusting that sequence in response to those steps with a specified range of times, and iterating the calculation over a plurality of possible sequences. The processor may also optimize the order in which samples are moved to minimize the total time required by the system to complete the procedures, for example by generating a plurality of possible sequences, evaluating each sequence for total expected time, and selecting the best sequence available.

In a preferred embodiment, the robotic device comprises a set of standardized packages, disposed by means of a set of spring locks on a set of standardized tiles and accessed by a set of standardized holders for standardized slides or slide pairs, having contents comprising a standardized reagent, chemoactive or bioactive compound or mixture, or buffer, and a set of preprogrammed assay protocols. A standardized workstation may also comprise another type of device for operating on sample slides (or other carrying media such as test tubes or wafers), such as a centrifuge, diffusion, distillation or other separation device, a DNA crosslinking device, an electroporator, a microwave device or other radiation source, an incubation oven or other heating unit, or a refrigeration element or other cooling unit. Because the packages, tiles, contents, and protocols are standardized or preselected, the operator may quickly insert the packages into the tiles, open the packages for operation, and select a preprogrammed assay protocol. All these operations may be performed quickly and may promote rapid and efficient operation of the robotic device.

In a preferred embodiment, the processor may comprise a graphic interface by which an operator may specify the steps of a procedure. A display of the grid locations may comprise symbols for the workstations, which an operator may identify with a pointing device such as a mouse. The operator may create or edit templates for workstations, create or edit lists of process steps for procedures, monitor the progress of ongoing procedures, or override the determination of what process steps to perform. For example, in a preferred embodiment, the operator may create a list of process steps for a procedure by selecting a sequence of workstations with the mouse, and associating timing or other information for each process step with the selected workstation. The operator may also choose to select a stored list of process steps for a procedure.

Thus, the invention provides apparatus and methods whereby a plurality of test procedures can be performed on several samples, e.g., through the use of time division multiplexing. The invention also provides apparatus for use in a laboratory for assisting in the performance of multiple tests which can be easily programmed by the operator to execute sequentially timed step procedures for a plurality of test samples. The invention also provides a flexible laboratory testing system which may use time division multiplexing to interleave the multiple steps of a plurality of test procedures to allow for a plurality of different procedures to be performed on several different test samples in parallel.

BRIEF DESCRIPTION OF THE DRAWINGS

FIGS. 3B-1, 3B-2, 3B-3, 3B-4, 3B-5, and 3B-6 show a standardized package for coupling to the tile.

FIGS. 3C-1a–3C-3z show first and second standardized slide holder for coupling slides to a compound or mixture in a package.

FIGS. 3D-1 and 3D-2 show a workstation having an incubation oven and a carrying medium for inserting slides or slide pairs.

FIG. 4 is a flowchart showing a time line for five tasks.

FIG. 5 is a flowchart illustrating multitasking of the tasks shown in FIG. 4.

FIG. 6 shows a multitask monitoring screen as viewed by an operator.

DESCRIPTION OF THE PREFERRED EMBODIMENT

Figure 1:
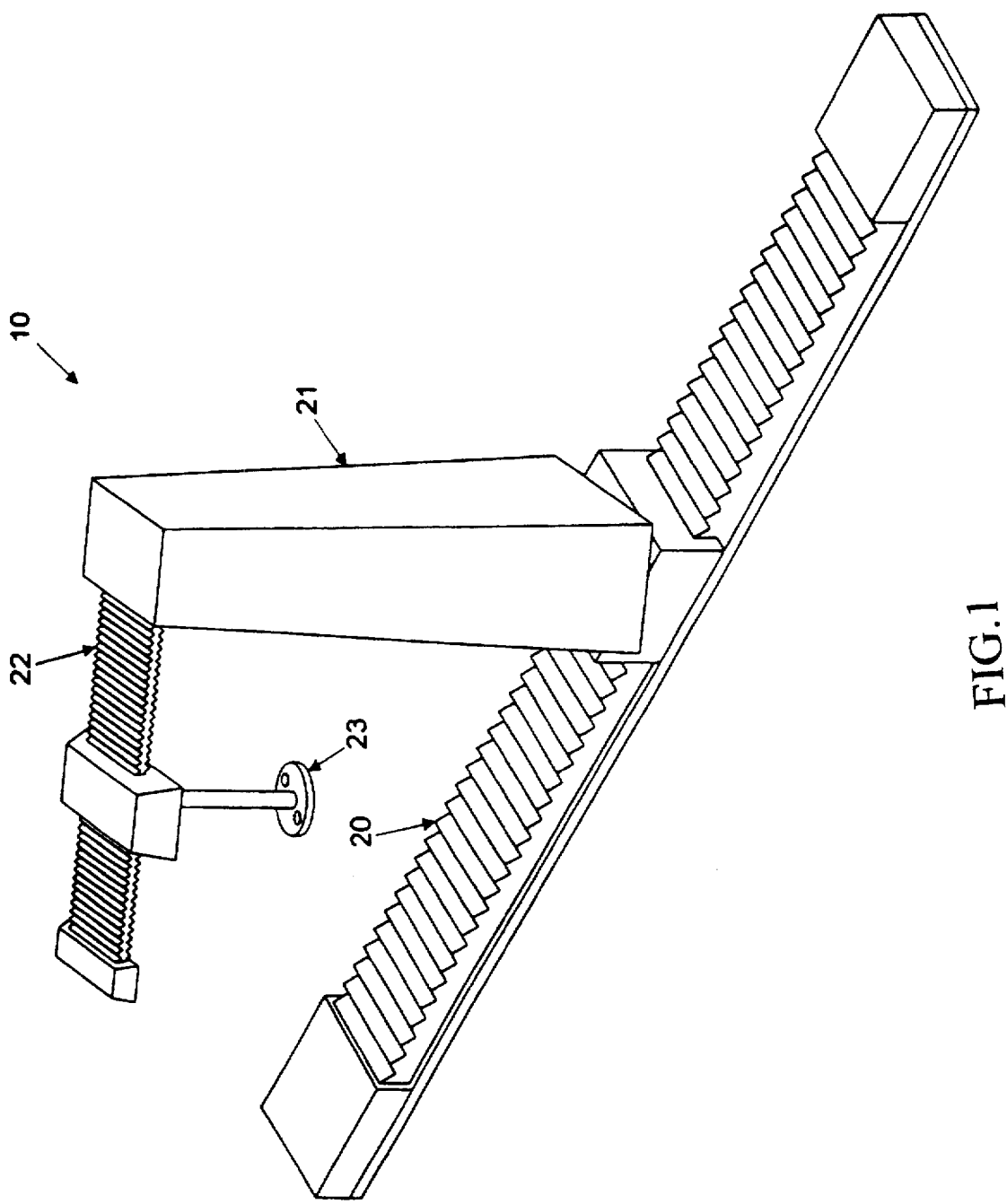
FIG. 1 shows a robotic device for use with the invention.

Inventions described herein may be made or used in conjunction with inventions described, in whole or in part, in the following patents, publications, or copending applications, all of which are hereby incorporated by reference as if fully set forth herein.

U.S. patent application Ser. No. 07/740,285, filed Aug. 5, 1991, in the name of inventors Steven A. Bernstein and Page A. Erickson, titled "Method and Apparatus for Automated Tissue Assay"; and U.S. patent application Ser. No. 08/218,143, filed Mar. 24, 1994, in the name of inventors Steven A. Bernstein and Page A. Erickson, titled "Method and Apparatus for Automated Tissue Assay".

In a preferred embodiment, a multiple axis bench top robot is located to reach peripheral auxiliary equipment disposed in the operational area of the robot. The robot may respond to the output of a PC type computer which utilizes process control programs and assay development software. Peripheral equipment, a plurality of work modules or workstations, is disposed in a grid like pattern around the bench top robot. The workstations may be disposed or arranged in any convenient pattern and may be represented by a template. Each grid location may contain the necessary equipment to perform a single step of a tissue assay procedure.

For example, a workstation at a grid position may contain a solution tray into which one or more slides may be immersed by the robotic equipment. The slide, or slides, could be immersed to a predetermined depth and retained in the solution tray for a precise time. It should be clear that each grid location may have a solution tray having different depths or different dimensions. Alternatively, a grid location could contain a slide holder or other peripheral equipment capable of performing a single function on the sample.

The robotic equipment or robotic arm may be controlled by a standard PC computer. The assay development software is graphic in nature and places a model of the peripheral grid on the screen of the computer. While each tissue assay may have all its steps preprogrammed the assay development software permits the steps of the procedure or the timing of the steps to be altered. The graphic nature of the presentation permits laboratory personnel to alter such elements without the necessity of relying on a computer or programming expert.

The process control software associated with the PC may monitor the progress of the assays, may permit manual override of an automatic operation, and most importantly, may permit scheduling of multiple assays simultaneously in parallel through the use of time interleaving of the various steps in the test procedures. Thus while sample #1 may be disposed at a workstation in a grid location where it undergoes a drying operation, sample #2 may be located in a tray containing a staining solution while sample #3 is undergoing a fixation step. The timing of each step is accurate and the system interleaves the steps and utilizes the "waiting" or processing time between steps in a single procedure to perform operational steps on other samples which may be undergoing completely different preparation.

Laboratory Bench and Robotic Device

Figure 2:
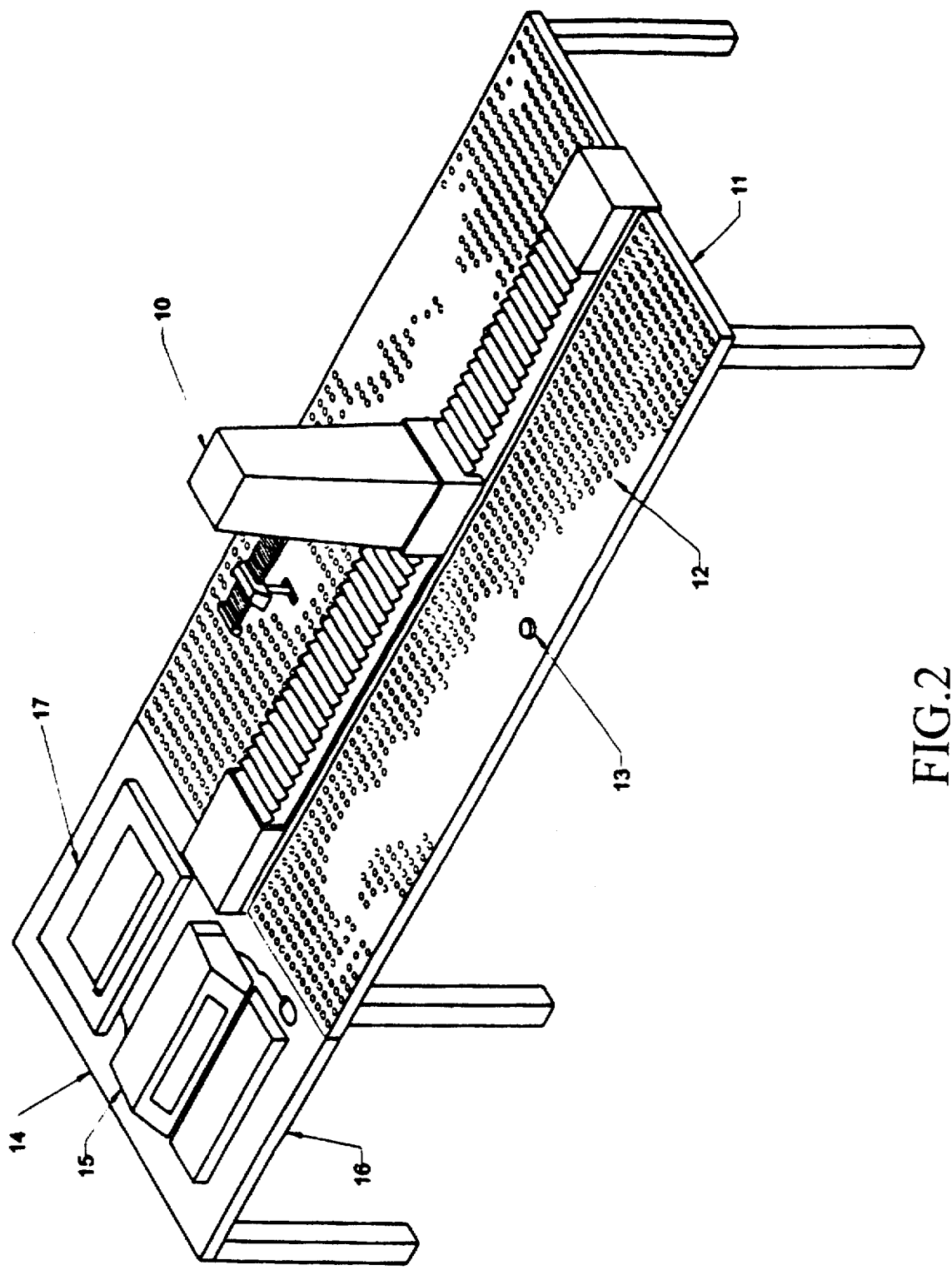
FIG. 2 shows a laboratory setup having robotic equipment like that shown in FIG. 1.

FIG. 1 shows a robotic device for use with the invention. FIG. 2 shows a laboratory setup having robotic equipment like that shown in FIG. 1. The equipment may include a robotic device 10 mounted on a standard laboratory bench top 11. The bench top 11 defines the operational area reachable by the robotic device 10. The bench top 11 may have integral therewith a plurality of locating elements such as holes 12. Alternatively, the locating elements may be disposed on a separate base disposed between the robotic device 10 and the laboratory bench top 11. A template may be used to represent the operational area and to assist in defining the exact location of each workstation.

Located on the bench top 11 are one or more work modules 13. A control station 14 is located adjacent to the laboratory bench 11. The control station 14 may include a typical PC type computer 15, such as an IBM-compatible computer having an Intel x86 processor, or a computer similar thereto, mounted on a desk 16 or other working surface. It would be clear to one of ordinary skill in the art, after perusal of the specification, drawings and claims herein, that other types of computers may be utilized to control the movement of the robotic arm 10. A printer 17 is shown although other peripheral equipments may be utilized in conjunction with the computer 15.

Referring to the bench top 11, a plurality of locating holes 12 are disposed at predetermined fixed locations relative to the robotic device 10. The locating holes are designed to receive modular workstations 13. Each modular workstation 13 is designed to be used in the performance of a particular process or step in one laboratory task or test procedure. Thus each function required to be performed in a task is associated with a work module 13 which has a predisposed known position on the work bench 11.

There are a number of methods by which the location of a particular work module 13 can be supplied to the computer 10. For example each work module 13 may include a floppy disk which would contain the physical characteristics of the work module, such as its height, width and length. The customized data for each module would be fed into the central processing unit of the computer and would query the operator, for example through a CRT display, to provide the location of the work module. The operator through the keyboard input would specify the location of the module on the locating grid. Thus for each work module or step of a task the computer would have stored in its memory the physical characteristics and location of the module.

In a preferred embodiment, the robotic device 10 is capable of travel in an X direction along a first cable driven bearing 20 (actuated by a first cable drive 20a). Disposed at right angle to and vertical with respect to the first cable driven bearing 20 is a second cable driven bearing 21 (actuated by a second cable drive 21a), capable of traversing the first cable drive 20a. Coupled to the cable drive 21a is a third cable driven bearing 22 (actuated by a third cable drive 22a) disposed at a right angle. A robotic hand 23 is mounted on cable drive 22 and comprises a spring loaded solenoid 23a coupled to a rubber securing ring 23b. The securing ring 23b is capable of coupling to a sample carrier 23c. The sample to be assayed (which may be a tissue sample) is mounted on the sample carrier 23c.

Thus the hand 23 on which the sample is mounted is capable of X movement along cable driven bearing 20, Y movement along cable driven bearing 21, and Z movement along cable driven bearing 22. The system illustrated is thus capable of motion relative to three axes. Although the system is illustrated using cable driven bearings 20, 21 and 22, it would be clear to those skilled in the art, after perusal of this application, that other robotic equipment could be provided that could decrease or increase the number of axes, that other techniques other than cable drives and cable driven bearings, (such as lead screws, gears, belts, or other devices) could be used, that such other equipment or techniques would be workable, and are within the scope and spirit of the invention.

Typically, the range of movement along the X axis may be about 76 inches, along the Y axis about 19 inches, and along the Z axis about 18 inches. Such a typical range of movement could provide approximately 15 cubic feet of operational area.

System Operation

In order to illustrate the operation of this invention, let it be assumed that the laboratory has five example tasks to accomplish, each having five example steps. For purposes of illustration, the five steps in each of the five tasks will be utilized to demonstrate the multitasking capabilities of the invention. The five tasks and the five steps of each of the tasks are shown in Table 1 herein.

TABLE 1

Five Tasks

Task #1 Basic Fuchsin Staining

Step #1 Buffer 1
Step #2 Buffer 2
Step #3 Basic Fuchsin
Step #4 Pad 1
Step #5 Buffer 2
Task #2 Azure II & Methylene Blue
Counterstaining Step #1 Azure II
Step #2 Pad 1
Step #3 Buffer 1
Step #4 Pad 1
Step #5 Methylene Blue

TABLE 1-continued

Five Tasks

Task #3 Tissue Fixation

Step #1 Isotonic Rinse
Step #2 Primary Fixative
Step #3 Buffer 1
Step #4 Buffer 2
Step #5 Secondary Fixative

Task #4 Immunocytochemistry

Step #1 Buffer 1
Step #2 Pad 1
Step #3 Blocking Antibody
Step #4 Pad 1
Step #5 Buffer 1

Task #5 Slide Silinizing

Step #1 APTES
Step #2 Toluene
Step #3 Water
Step #4 Pad 1
Step #5 Oven

It is apparent from Table 1 that some of the tasks utilize the same steps such as Pad 1 or Buffer 1. If these steps were to be carried out in accordance with the principles of this invention, it would be necessary to provide only 14 work modules even though 25 steps were being performed. Disposed on the grid would be a separate work module for each of the 14 different steps listed above. Thus there would be a Pad 1 module to be used in carrying out seven of the above steps. Alternatively, the user could provide multiple modules, each capable of performing the pad function. A Buffer 1 module would be used for five of the steps and a Buffer 2 module for two of the steps. Each of the remaining steps would have a module disposed on the grid to perform the necessary work associated with the step.

It is often essential that the step of the task be performed within certain time limits. The timing of some steps can be critical. FIG. 4 is a flowchart showing a time line for the five steps of the tasks in Table 1. It should be noted that Task #1, Step #1 commences at 9:00 and has a duration of approximately 15 minutes, inclusive of the time necessary to transport the sample to the location where Step #2 is performed. Thus Step #2 will commence at approximately 9:15. It should be noted that the timing for the start of Step #2 has some leeway in that it can commence between 9:15 and 9:18, providing leeway of three minutes. Step #2 has a duration of approximately 11 minutes and the sample is transported to the location where Step #3 will be performed. The time for performing Step #3 is critical as indicated by the lack of interval for the starting times. Step #3 must commence at 9:26. Fourteen minutes later the sample is undergoing Step #4, which can commence any time between 9:40 and 9:50. The last Step #5 is performed at 9:51. It should be noted that if each Step is commenced at the outer time limit Step #5 may not begin until 10:22.

In a similar manner it can be determined from FIG. 4 that the five steps of Task #2 may consume 1 hour 34 minutes, Task #3, 1 hour 9 minutes, Task #4, 1 hour 17 minutes, and Task #5, 1 hour 16 minutes. Thus if the five steps of the tasks shown were to be performed sequentially the total time to completion would be 6 hours 38 minutes.

Referring to FIG. 5, the multitasking method of this invention is therein illustrated to show the time interleaving of the steps of the multiple tasks. Assuming again for purposes of illustration and simplification of explanation that we are desirous of performing the same five steps for the same five tasks. Under the control of the computer the robotic hand would be commanded to obtain sample #1 or alternatively the sample could be brought to the robotic hand and for grasping. The hand retaining the grasped sample would move the sample to the location of the work module for Task #1, Step #1, i.e., Buffer 1. The sample would be freed from the hand and left at the work module. The hand would proceed to the location of sample #2 where it would grasp the sample and carry it to the work station where Task #2, Step #1 would be performed.

Each of the five samples would in turn be grasped by the robotic hand and transported to the work module associated with the first step of the task to be performed on each sample. It should be noted that the design of the Buffer and Pad work modules permit the simultaneous treatment of at least two samples from different tasks. Alternatively, two work modules could be provided so that each sample could be treated in a different module.

After locating sample #5 in the Task #5, Step #1 module, the robotic hand returns to the module for Task #5, Step #1 and gasps the sample #5 and transports it to the module for Task #5, Step #2. Following the path illustrated in FIG. 5, the hand proceeds from the Task #5, Step #2 module to Task #3, Step #3 module where it grasps sample #3 and transports it to Task #3, Step #2 module where the sample is deposited. The hand then returns to the location of the first sample which is in the module associated with Task #1, Step #1 and takes it to the module for Task #1, Step #2. The hand returns to the location sample #4 and carries it to Task #4, Step #2 and then at the appropriate time transports the same sample to Step #3 of Task #4.

At this point in the operation of the system, the computer detects that Task #1, Step #3 and Task #2, Step #2 are both scheduled to start at the same time, 9:26. In order to resolve the conflict the system utilizes a technique, herein termed "fuzzy timing", to process the control of the robotic hand and optimize the process. Fuzzy timing may comprise the window of time during which each process (Task) step may occur without affecting the process results. Some steps of a process may be critically timed, i.e., the time required for that step is exact, such as Task #1, Step #3 in FIG. 5, but in general most steps a process the timing is less critical and may comprise any amount of time within a known range and thus are noncritical in their timing, such as Task #2, Step #2, which has a window of four minutes, as shown in FIG. 5. The system of this invention uses these windows of time to advantage as to optimize (minimize) the time necessary to complete the multiple tasks.

The use and advantages of "fuzzy timing" can be illustrated by considering two different tasks, each having a process step terminating at the same time or within moments of the another. Assuming that both steps are critically timed in so far as the termination time is concerned, it is apparent that both samples from the two different steps can not be moved to the next step in each process simultaneously since concurrent movement of two samples is not within the capabilities of this embodiment. Thus it is necessary to adjust the starting times for the two steps relative to each other so that the ending times will allow for the movement of each sample to its next process step. While this can be done quite easily, it is clear that the mere adjustment of a starting time for a step in the process may well cause other timing conflicts. It is possible that under such conditions the system could not support simultaneous throughput of multiple processes unless the timing was altered.

Fuzzy timing allows the system additional flexibility since by providing a window of time at each noncritically timed process step, conflicts will be minimized through the adjustment of timing at the step level, rather than by shifting the timing of the whole process or task.

Standardized Chemicals and Packages

Figures 1, 3A:
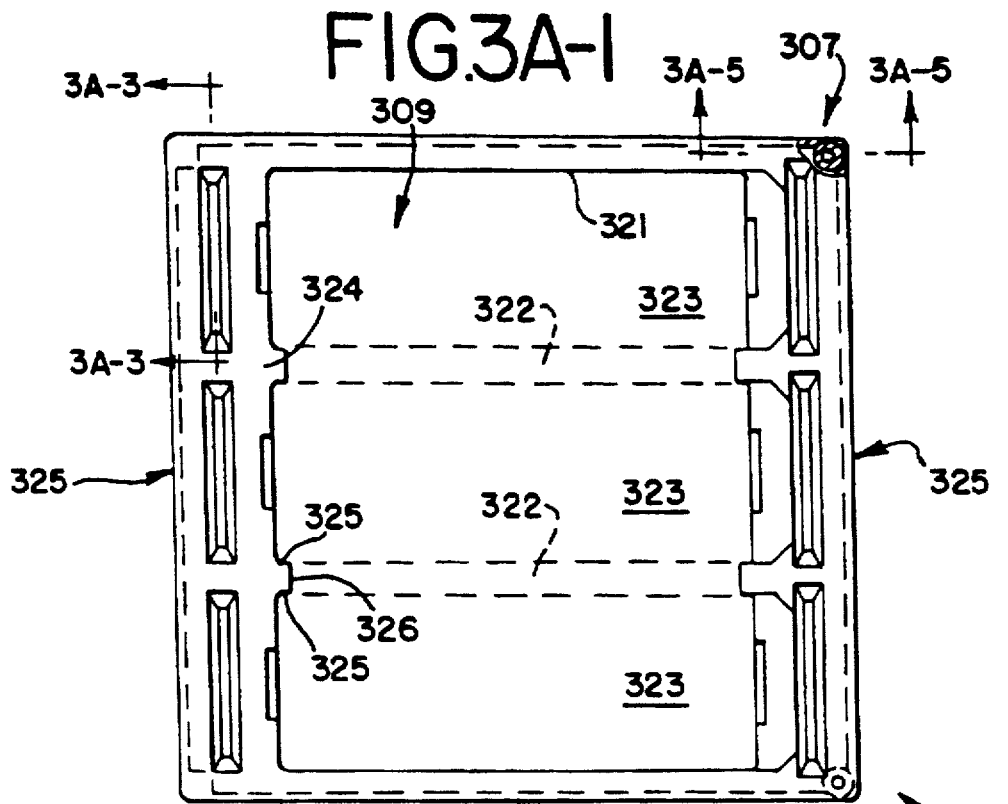
FIG. 3A shows a standardized tile for coupling to the robotic device.
Figures 2, 3A:
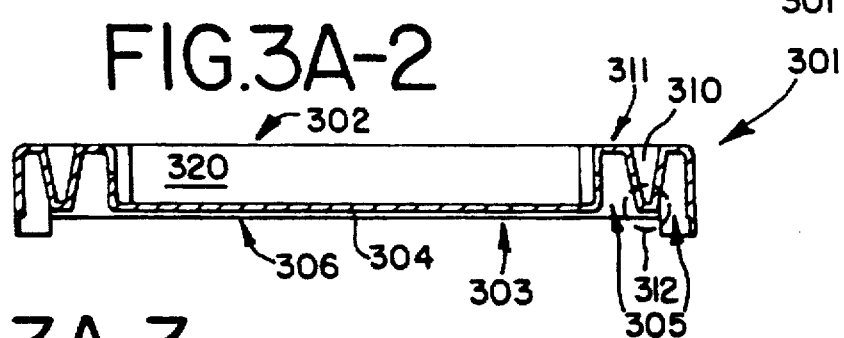

FIG. 3A shows a standardized tile for coupling to the robotic device.

As described herein, the robotic device 10 may be mounted on a bench top 11 having a plurality of locating elements such as holes 12 and having a plurality of work modules 13 disposed thereon.

In a preferred embodiment, each work module 13 comprises one or more tiles 301, each tile 301 comprising a molded plastic piece having a top face 302 and a bottom face 303.

The bottom face 303 of the tile 301 comprises a relatively flat plastic surface 304, possibly having one or more bottom indentations 305 and bottom ribs 306, and having a set of receiving wells 307 for insertion of a corresponding set of fasteners 308. As shown in FIG. 3A, the fasteners 308 fit through a set of holes 12 for a designated location on the bench top 11, and are coupled to the receiving wells 307 for fastening the tile 301 to the top surface of the bench top 11.

In a preferred embodiment, the fasteners 308 comprise screws, but those skilled in the art will recognize, after perusal of this application, that other types of fasteners would also be workable with the devices and substances described herein, and are within the scope and spirit of the invention.

The top face 302 of the tile 301 comprises a set of receiving areas 309 for insertion of a corresponding set of standardized packages 401. The top face 302 also comprises a set of one or more top indentations 310 and top ribs 311. A set of holes 312 are disposed in at least some of the top indentations 310, so that liquids in those top indentations 310 may drain. Each receiving area 309 comprises a depression 320, into which a package 401 (FIG. 3B) may be placed.

Each depression 320 comprises a pair of side walls 321 disposed parallel to each other, a pair of intermediate barriers 322 disposed so as to divide the depression 320 into a set of three subdepressions 323, each intermediate barrier 322 having a pair of stubs 324. Each pair of stubs 324 is aligned with each other and disposed parallel to the side walls 321, so that a package 401 may be snugly fitted into one of the three subdepressions 323.

Each stub 324 comprises a first and second stub side 325 and a stub end 326. The stub sides 325 for the stub 324 are disposed parallel to the stub sides 325 of the matching stub 324, and parallel to the side walls 321. The stub end 326 for the stub 324 is generally disposed so that the stub 324 is relatively short compared with the package 401.

When a package 401 is fitted into a side one of the three subdepressions 323, it is disposed with a first package side 402 (FIG. 3B) disposed next to a first side wall 321 and with a second package side 402 disposed next to one of the stubs 323, in particular, next to one of the stub sides 324. A first end of the second package side 402 is disposed next to a first stub 323, while a second end of the second package side 402 is disposed next to a second stub 323, the second stub 323 being the matching stub 323 aligned with the first stub 323.

Alternatively, a package 401 may be fitted into a center one of the three subdepressions 324. In this case, it is disposed with a first package side 402 disposed next to a first pair of stubs 323, and a second package side 402 next to a second pair of stubs 323. A first end 403 (FIG. 3B) of the second package side 402 is disposed next to a first stub 323 in its pair, while a second end 403 of the second package side 402 is disposed next to a second stub 323 in its pair, the second stub 323 being the matching stub 323 aligned with the first stub 323.

Each subdepression 323 comprises a pair of receiving holes 325 for insertion of a corresponding lever 404 (FIG. 3B) and a corresponding spring lock 405 (FIG. 3B) of the package 401 to be disposed in the subdepression 323. When the package 401 is fitted into the subdepression 323, the lever 404 of the package 401 is disposed in a first one of the receiving holes 325, and the spring lock 405 of the package 401 is disposed in the second one of the receiving holes 325.

Figures 3, 3A:
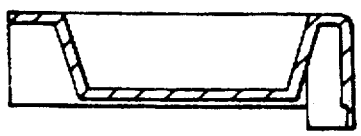
Figures 3, 3A, 4, 5:
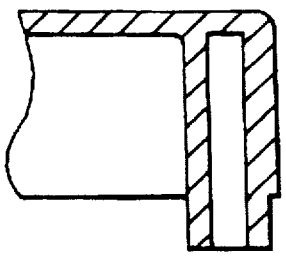
Figures 3, 3A, 4:
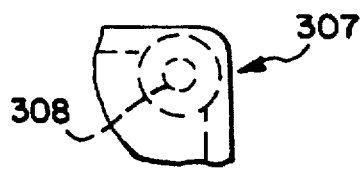
Figures 1, 3B:
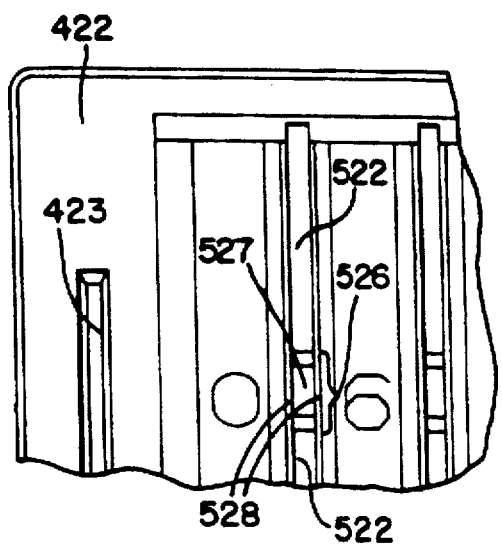
Figures 3, 3B:
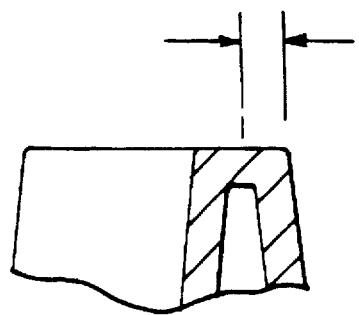
Figures 2, 3B:
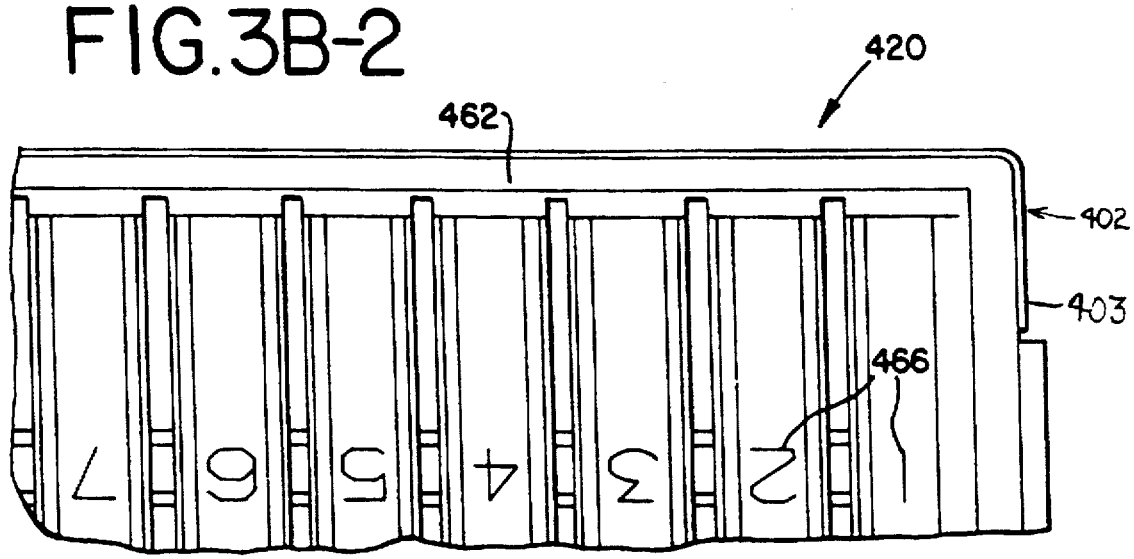

FIG. 3B (comprising 6 parts, individually FIGS. 3B-1, 3B-2, 3B-3, 3B-4, 3B-5, and 3B-6) shows a standardized package for coupling to the tile.

In a preferred embodiment, a standardized package 401 comprises a molded plastic tray 406 and a thin cover 407 affixed to the tray 406, such as by a heat weld, a glue, or other known means. In a preferred embodiment, the thin cover 407 may comprise a plastic or metallic sheet 408, laminated on an outside side 409 with plastic and printed thereon with identifying information, and coated along an edge area 410 on an inside side 411 with a fixative 412 and affixed by means of that edge area 410 to a corresponding tray surface 413.

In a preferred embodiment, the fixative 412 comprises a heat weld, but those skilled in the art will recognize, after perusal of this application, that other types of bonding techniques would also be workable, such as crimping or welding, or glue, and are within the scope and spirit of the invention.

The tray 406 comprises a tray frame 420, having a rectilinear shape with a top surface 421. The top surface includes the tray surface 413 for bonding with the cover 407, and also includes a handle region 422 with a hole 423 disposed therein.

The cover 407 also comprises a cover lip 414 disposed on at least one end of the package 401, having a sufficient size to be grasped by an operator and removed from the tray 406.

The tray frame 420 comprises a pair of side surfaces 424, disposed perpendicular to the top surface 421. The side surfaces 424 form the package sides 402 and the ends 403 of the packet sides 402.

The tray frame 420 comprises a first end surface 425, disposed perpendicular to the top surface 421 and to the side surfaces 424, and forming a box shape underneath the handle region 422 and the hole 423, providing additional sturdiness in that region.

The tray frame 420 comprises a second end surface 426, disposed perpendicular to the top surface 421 and to the side surfaces 424, and having the spring lock 405 disposed thereon.

The tray frame 420 comprises a set of tray ribs 427, disposed underneath the top surface 421 and near the side surfaces 424, providing additional sturdiness to the tray 406 and the side surfaces 424.

The tray frame 420 is coupled to a well frame 440, which comprises a rectilinear shape having a pair of well sides 441, a well bottom 442, a set of wells 460, a first well end 443 near the first end surface 425, and a second well end 444 near the second end surface 426.

The wells 460 each comprises a truncated wedge shape, having a single well bottom 461 that is U-shaped, with the plane of the U-shape parallel to the side surfaces 424, and a pair of single well sides 462 that are flat and each have a trapezoidal shape. Each single well bottom 461 comprises a set of three relatively straight surfaces, a well horizontal bottom 463 that is relatively flat and horizontal (and may comprise a V shape with a arms of the V shape disposed about 2.5 degrees from horizontal), and a pair of well semibottoms 464 that are flat and disposed at an angle of about 9.5 degrees from the vertical.

The single well bottoms 461 are disposed in a continuous sequence so as to merge to form the well bottom 442. The well bottom 442 is therefore formed without seams and with ridges 465 formed by well semibottoms 464 adjacent to each other.

The single well sides 462 are disposed in a continuous sequence so as to merge to form the well sides 441. The well sides are therefore formed without seams and without ridges.

Each well 460 is formed with a molded label 466 that is unique within the package 410. In a preferred embodiment, the labels 466 are formed by molding the plastic of the tray 406, but those skilled in the art will recognize, after perusal of this application, that the labels could be workably formed by alternative means, such as etching, printing, or scoring, and that such alternative means are within the scope and spirit of the invention. In a preferred embodiment, the labels 466 may each comprise a single digit "0", "1", "2", "3", "4", "5", "6", "7", "8", or "9". Alternatively, the number "10" may be substituted for the digit "0".

A first well 460 with a label 466 of "0" is disposed near the first end surface 425 and has the lever 404 disposed thereon.

A second well 460 with a label 466 of "1" is disposed near the second end surface 426 and has a set of end ribs 467 disposed thereon.

The lever 404 comprises a right-angled lever lip 480, having a first lever surface 481 and a second lever surface 482, supported by a set of lever ribs 483 disposed between the first lever surface 481 and the first well 460 and underneath the second lever surface 482. The lever lip 480 is disposed at parallel to the first end surface 425 and sized to fit into the corresponding receiving hole 325. In a preferred embodiment, the first lever surface 481 has at least one lip hole 484 disposed thereon, to promote mating at a surface of the tile 301 near the receiving hole 325.

The spring lock 405 comprises a right-angled spring lip 500, having a first spring surface 501 and a second spring surface 502, supported by a set of first spring ribs 503 underneath the second spring surface 502. The first spring surface 501 comprises a section of the second end surface 426 having a pair of cuts 504 disposed thereon, a reinforced spring base 505 disposed at a base of the pair of cuts 504, and a pair of second spring ribs 506 disposed underneath the second spring surface 426 near the cuts 504. The spring lip 500 is disposed in parallel to the second end surface 426 and sized to fit into the corresponding receiving hole 325.

An inside surface 520 of the tray 406 comprises a set of inside wells 521 corresponding to the wells 460. Each adjacent pair of inside wells 521 is separated by a well divider 522. Each well divider 522 comprises a U-shaped, with the plane of the U-shape perpendicular to the side surfaces 424, and having a taper from thicker near a bottom end 523 disposed near the bottom 524 of the inside wells 521 to thinner near a top end 525 disposed farther from the bottom 524 of the inside wells 521.

Each well divider 522 comprises a center 526, at a bottom curve of the U-shape, that has an indentation 527, thus forming two lips 528 disposed between each adjacent pair of inside wells 521.

Each well divider 522 comprises a well top 527, at a pair of top ends 528 of the U-shape, disposed with a gap 529 between the well top 527 and the cover 407.

In a preferred embodiment, the well dividers 522 are sized so that each inside well 521 may hold 750 microliters (¾ of a milliliter) of liquid without spilling over to an adjacent inside well 521. However, if the amount of liquid in an inside well 521 exceeds 750 microliters, the liquid will spill over the bottom curve of the U-shape of the well divider 522, and thus spill into the adjacent inside well 521.

In a preferred embodiment, the robotic device 10 operates by orienting a slide 540 with a specimen 541 vertically for insertion into the inside well 521, i.e., with the flat surfaces of the slide 540 being perpendicular to a plane of the ground. When the slide 540 is inserted into the inside well 521, a liquid content 542 of the inside well 521 will coat the specimen 541 by means of capillary action.

This capillary action is particularly promoted if the slide 540 is coupled to a second slide 540 to form a slide pair 543, with the specimen 542 sandwiched between the slide 540 and the second slide 540 of the slide pair 543, and with the slide 540 and the second slide 540 maintained a selected separation distance apart of preferably about 146 microns +/−12 microns. However, those skilled in the art will recognize, after perusal of this application, that slides of differing sizes and selected separation distances would be workable, and are within the scope and spirit of the invention. For example, a selected separation distance for a slide 540 or a slide pair 543 for frozen tissue may comprise a substantially larger size, such as about 200 microns. A preferred embodiment of the slide pair 543 is shown in one or more of the following U.S. patents, hereby incorporated by reference as if fully set forth herein: U.S. Pat. Nos. 4,731,335; 4,777,020; 4,798,706; 4,801,431; 4,975,250; 5,002,736; 5,023,187; and 5,116,727, and may be used in conjunction with inventions therein.

It has been found by the inventors that the selection of the particular volume, 750 microliters, for each inside well 521 is particularly advantageous. This selected volume of liquid is generally sufficient to perform all the steps of typical immunohistochemical stains and other assay protocols (generally, with this selected volume of liquid, slides 540 or slide pairs 543 may be inserted into the inside well up to about three times). However, this selected volume of liquid is not so large that nonspecimen parts of slides 540 or slide pairs 543 (such as the back or sides) are regularly excessively contaminated. This selected volume of liquid also has the advantage, particularly when held in an inside well 521 having a single well bottom 461 with relatively steep sides (formed by the well horizontal bottom 463 and the well semibottoms 464), that there is a reduced surface/volume ratio. This provides for lesser evaporation of the liquid in the inside well 521.

It has also been found by the inventors that the selected shape of the inside well 521 is particularly advantageous. This particular shape promotes self-levelling and reduced evaporation, as noted herein. Moreover, this particular shape promotes centering within the inside well 521 of small amounts of liquid (about 150 microliters), due to surface tension repulsion of the liquid by the well semibottoms 464. Centering of the liquid promotes capillary action when a slide 540 or slide pair 543 is inserted into the inside well 521.

Preferred filling amounts for content of the inside well 521 are about 350 microliters when the compound or mixture is not too expensive, and about 200 microliters when the compound or mixture is relatively expensive (or when other reasons exist to restrict the amount, such as the compound or mixture being dangerous in quantity).

Preferred dimensions and tolerances for tiles 301 and packages 401 are shown in FIGS. 3A and 3B.

Figures 1A, 3C:
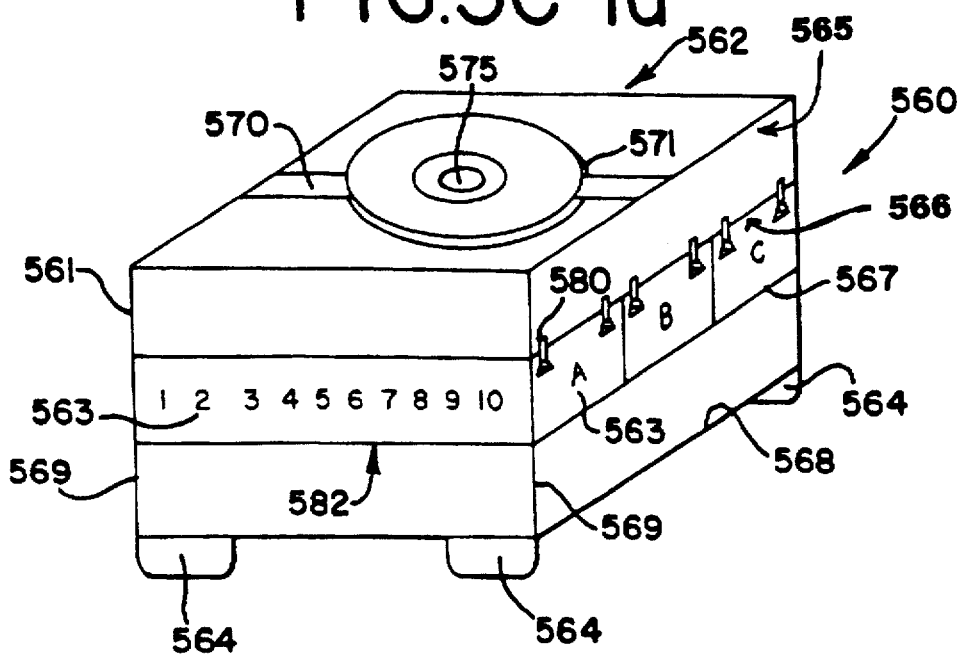
Figures 1B, 3C:
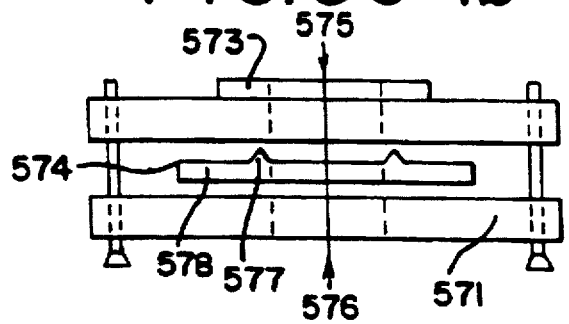
Figures 2, 3C:
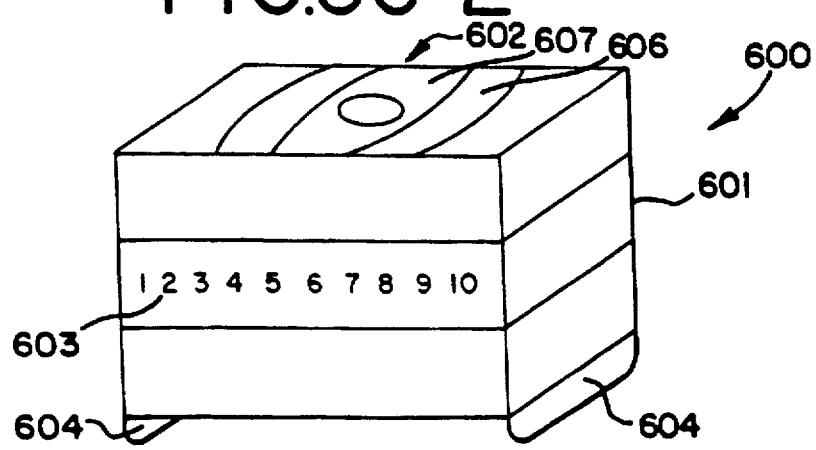
Figures 3A, 3C:
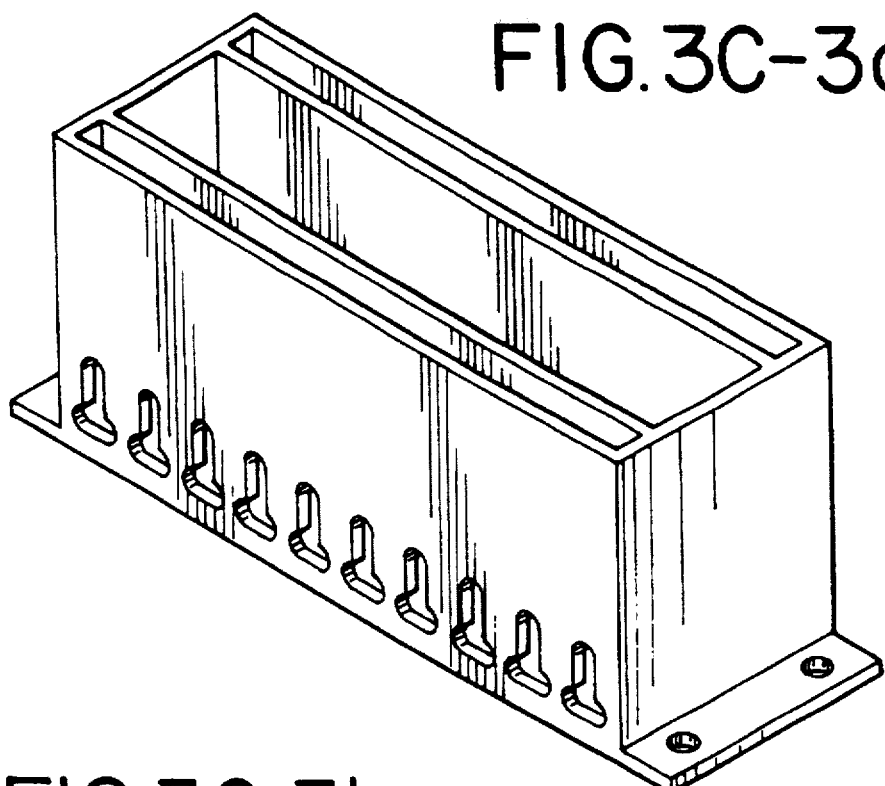
Figures 3B, 3C:
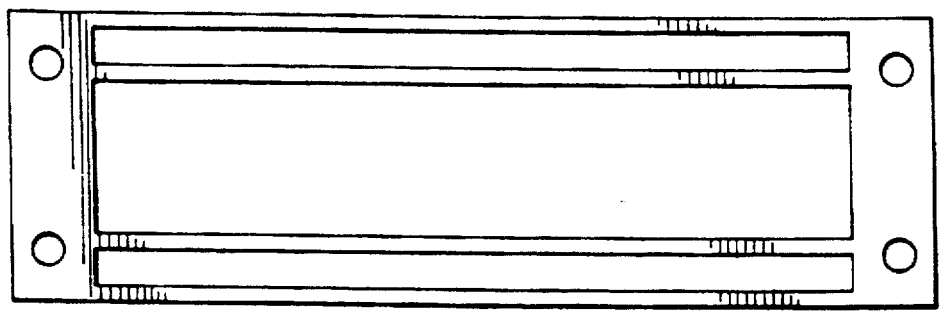
Figure 3C:
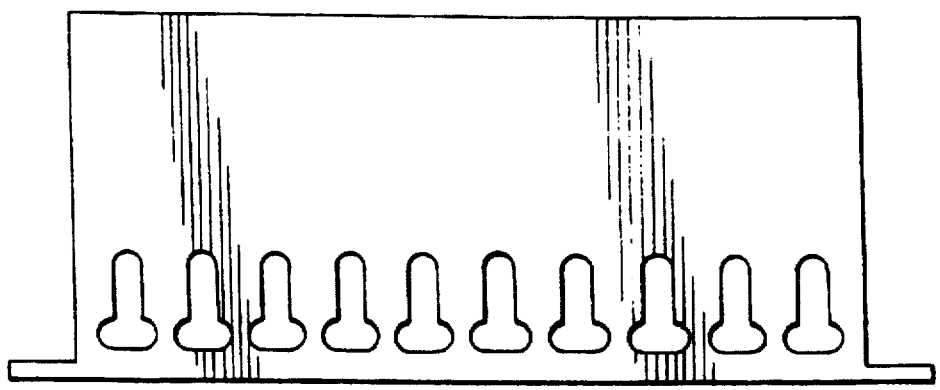

FIGS. 3C-1a–3C-3z show first and second standardized slide carriers for coupling slides to a compound or mixture in a package.

In a preferred embodiment, a first standardized slide carrier 560 comprises a frame 561, a coupling ring 562, a set of slide frames 563, and a set of feet 564. The frame 561 comprises a metal frame comprising a set of four horizontal elements (a top 565, a slide top 566, a slide bottom 567, and a bottom 568), and a set of four support posts 569. The top 565, slide top 566, slide bottom 567, and bottom 568 are coupled and supported by the four support posts 569, to make the frame 561 rigid and sturdy.

The coupling ring 562 is coupled to the top 565 by means of a pair of ring supports 570, that connect the coupling ring 562 to the rest of the top 565. The coupling ring 562 is a roughly circular element and has a similarly shaped ring base 571 underlying it and coupled to it by means of screws 572 disposed through the ring supports 570 with their axes aligned vertically. The coupling ring 562 also has a ring bumper 573 disposed on top and coupled to it by means of glue or another fastening technique.

The coupling ring 562 comprises a plastic disk 574, defining a circular hole 575 (smaller to and aligned with a circular hole 576 defined by each of the coupling ring 562, the ring base 571, and the ring bumper 573), and having a circular raised lip 577 surrounding the hole 576. The disk 574 also comprises a circular flat portion 578 disposed between the coupling ring 562 and the ring base 571, sufficiently large so that the disk 574 cannot fall out from between the two. The coupling ring 562 is thus disposed and shaped so the robot's rubber securing ring 23b may couple thereto and form a firm (but easily detachable) coupling.

If the robot's rubber securing ring 23b is slightly misaligned from the disk 574 in the X or Y direction or both, the disk 574 will realign within the rubber securing ring 23b by sliding within the region defined between the coupling ring 562 and the ring base 571. The rubber securing ring 23b and the disk 574 may thus couple anyway despite slight misalignment in the X or Y direction or both, up to about 2 mm in a preferred embodiment. Similarly, if the robot's rubber securing ring 23b is slightly misaligned from the disk 574 in the Z direction, an outside part of the rubber securing ring 23b will bump against the ring bumper 573, so the rubber securing ring 23b and the disk 574 may thus couple anyway despite slight misalignment in the Z direction, up to about 2 mm in a preferred embodiment.

The slide frames 563 (preferably there are three of them) are coupled to the slide top 566, by means of a set of screws 580 disposed with their axes aligned vertically. Each slide frame 563 comprises a set of slide positions 581 for holding standardized slides 540 or slide pairs 543. The slide bottom 567 is disposed to support the slide frames 563 relatively tightly. An underside 582 of the slide bottom 567 is labelled with a set of letters 583 "A", "B", and "C", disposed with one letter near each slide frame 563, and a set of digits 584 "1", "2", "3", "4", "5", "6", "7", "8", "9", and "0", disposed with one digit near each slide position 581 in each slide frame 563. A preferred embodiment for the slide frame 563, and related inventions, are shown in one or more of the following U.S. Patents, hereby incorporated by reference as if fully set forth herein: U.S. Pat. Nos. 4,731,335; 4,777,020; 4,798,706 4,801,431; 4,975,250; 5,002,736; 5,023,187; and 5,116,727, and may be used in conjunction with inventions shown therein.

The set of feet 564 (preferably there are four of them) are coupled to the frame bottom 568, by means of being integratedly formed therewith. The feet 564 each comprise a wedge-shaped element 590, with a relatively thicker top end 591 and a relatively thinner bottom end 592, shaped and sized to fit into the top indentations 310 in the top face 302 of the tile 301 with a bit of extra space.

If, when the robot hand 23 deposits the slide carrier 560 onto the tile, the slide carrier's feet 564 are slightly misaligned from the tile's top indentations 310 in the X or Y direction or both, the wedge-shaped element 590 will realign within the top indentations 310 by force of the weight of the slide carrier 560, so the slide carrier's feet 564 and the top indentations 310 may thus couple anyway despite slight misalignment in the Z direction, up to about 2 mm in a preferred embodiment. Similarly, if the slide carrier's feet 564 are slightly misaligned from the top indentations 310 in the Z direction, the slide carrier 560 will fall into the top indentations 310, so the slide carrier's feet 564 and the top indentations 3120 may thus couple anyway despite slight misalignment in the Z direction, up to about 2 mm in a preferred embodiment.

In a preferred embodiment, a second standardized slide carrier 600 also comprises a frame 601, a coupling ring 602, a slide frame 603, and a set of feet 604. The second standardized slide carrier 600 comprises a similar structure to the first standardized slide carrier 560.

The first standardized slide carrier 560 comprises a generally cubic shape and is adapted for holding a set of three slide frames 563, each with 10 slide pairs (i.e., a total of 60 slides). However, the second standardized slide carrier 600 comprises a rectilinear shape and is adapted for holding a slide frame 603 with 10 slide pairs (i.e., 20 slides).

The first standardized slide carrier 560 comprises a roughly circular coupling ring 562, coupled to the top 565 by means of a pair of ring supports 570, which has a similarly shaped ring base 571 underlying it, and which also has a ring bumper 573 disposed on top. However, the second standardized slide carrier 600 comprises a coupling ring 602 that is integrated into the rest of a top 605 and is thus rectilinear, which has a similarly shaped ring base 606 underlying it, and which also has a ring bumper 607 disposed on its top. The ring bumper 607 is roughly circular but shaped to match the shape of the second standardized slide carrier 600.

The first standardized slide carrier 560 preferably comprises a set of three slide frames 563. However, the second standardized slide carrier 600 preferably comprises a single slide frame 608 having a plurality of slide positions 609. The underside 610 of the slide frame 608 is not labelled; rather, a pair of sides 611 of the slide frame 608 are labelled with a set of integers 612 "1", "2", "3", "4", "5", "6", "7", "8", "9", and "10", disposed with one digit near each slide position 609 in the slide frame 608.

The first standardized slide carrier 560 preferably comprises a set of four feet 564. However, the second standardized slide carrier 600 preferably comprises a set of only two feet 613.

Multiple page FIG. 3C-3, comprising 13 pages, shows detailed parts drawings for the first standardized slide carrier 560 and the second standardized slide carrier 600.

Workstation Devices

In addition to packages 401, the tile 301 at a workstation 13 may be coupled to another type of device for operating on samples, whether carried by slides 540, slide pairs 543, or another carrying medium such as a beaker, test tube or wafer. In a preferred embodiment, the tile 301 at a workstation 13 may be coupled to one or more of the following devices:

The workstation 13 may comprise a centrifuge, a diffusion device, a distillation device, or other separation device.

The workstation 13 may comprise a DNA crosslinking device.

The workstation 13 may comprise an electroporator.

The workstation 13 may comprise a laser device or other optical device.

The workstation 13 may comprise a microwave device, a shielded radioactive sample, or other radiation source, such as a source of electromagnetic or ionic radiation.

The workstation 13 may comprise an incubation oven or other heating unit.

The workstation 13 may comprise a refrigeration element or other cooling unit.

Figures 3C, 3D, 3E, 3F, 3G, 3H, 3I, 3J, 3K, 3L, 3M, 3N, 3O:
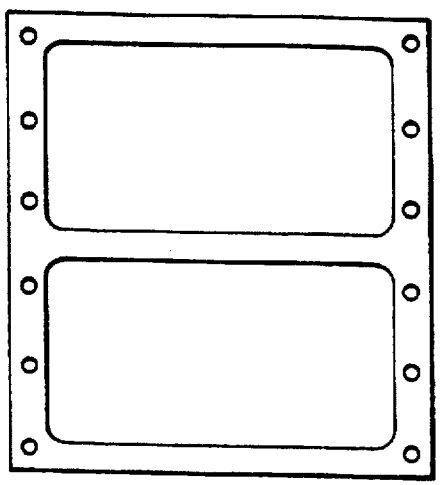
Figures 3C, 3P:
Figures 3C, 3Q:
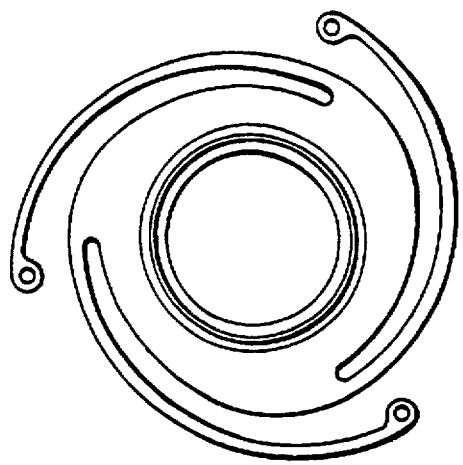
Figures 3C, 3R:
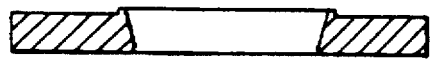
Figures 3C, 3S:
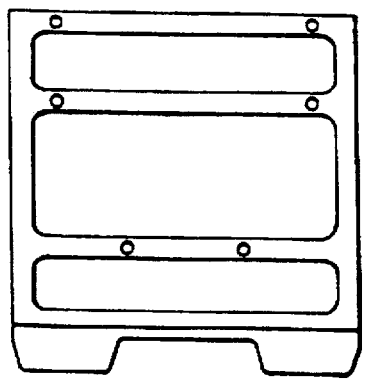
Figures 3C, 3T:
Figures 1, 3D:
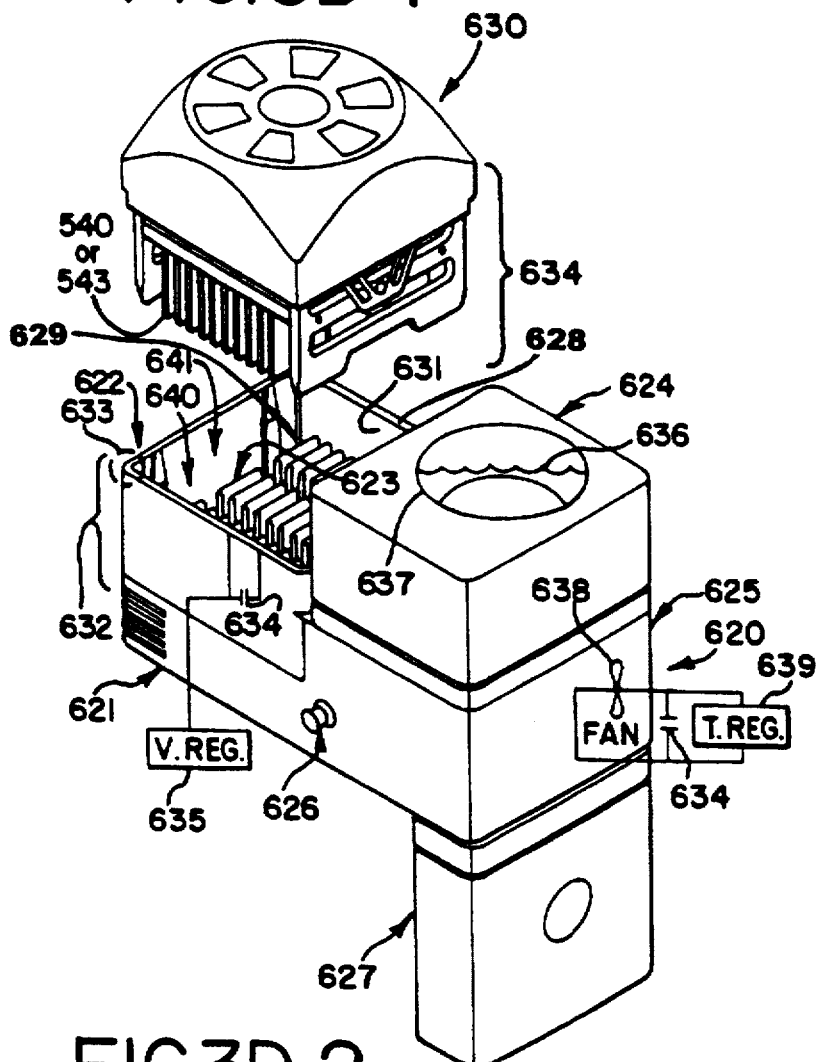
Figures 2, 3D:
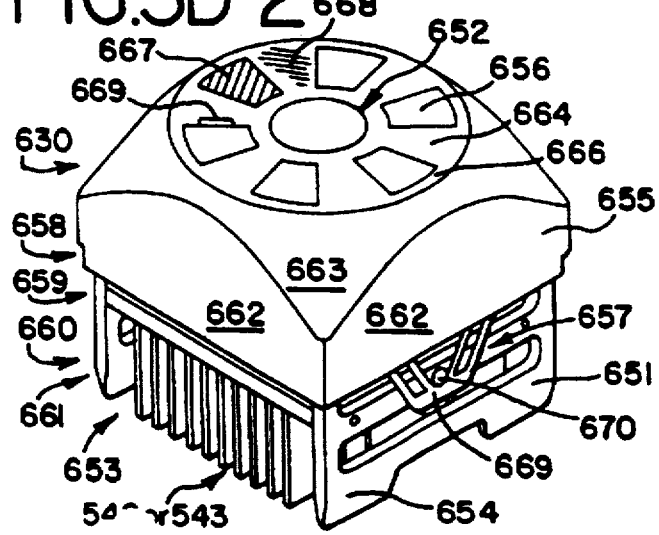
Figure 3E:
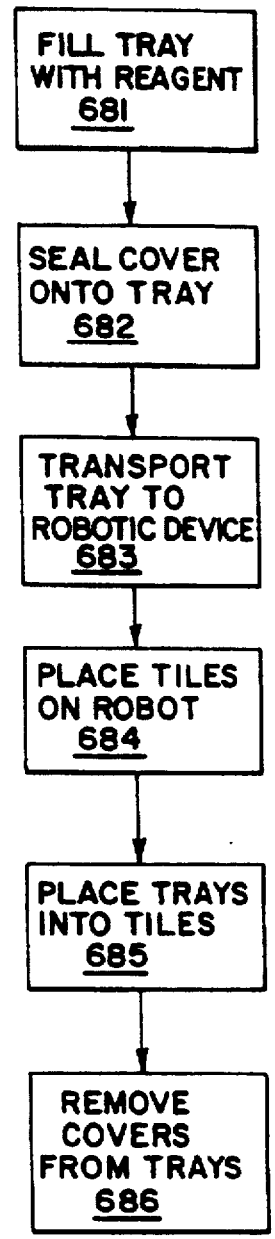
FIG. 3E is a flowchart of a preferred method of operating the robotic system with standardized packages and contents.
Figure 4:
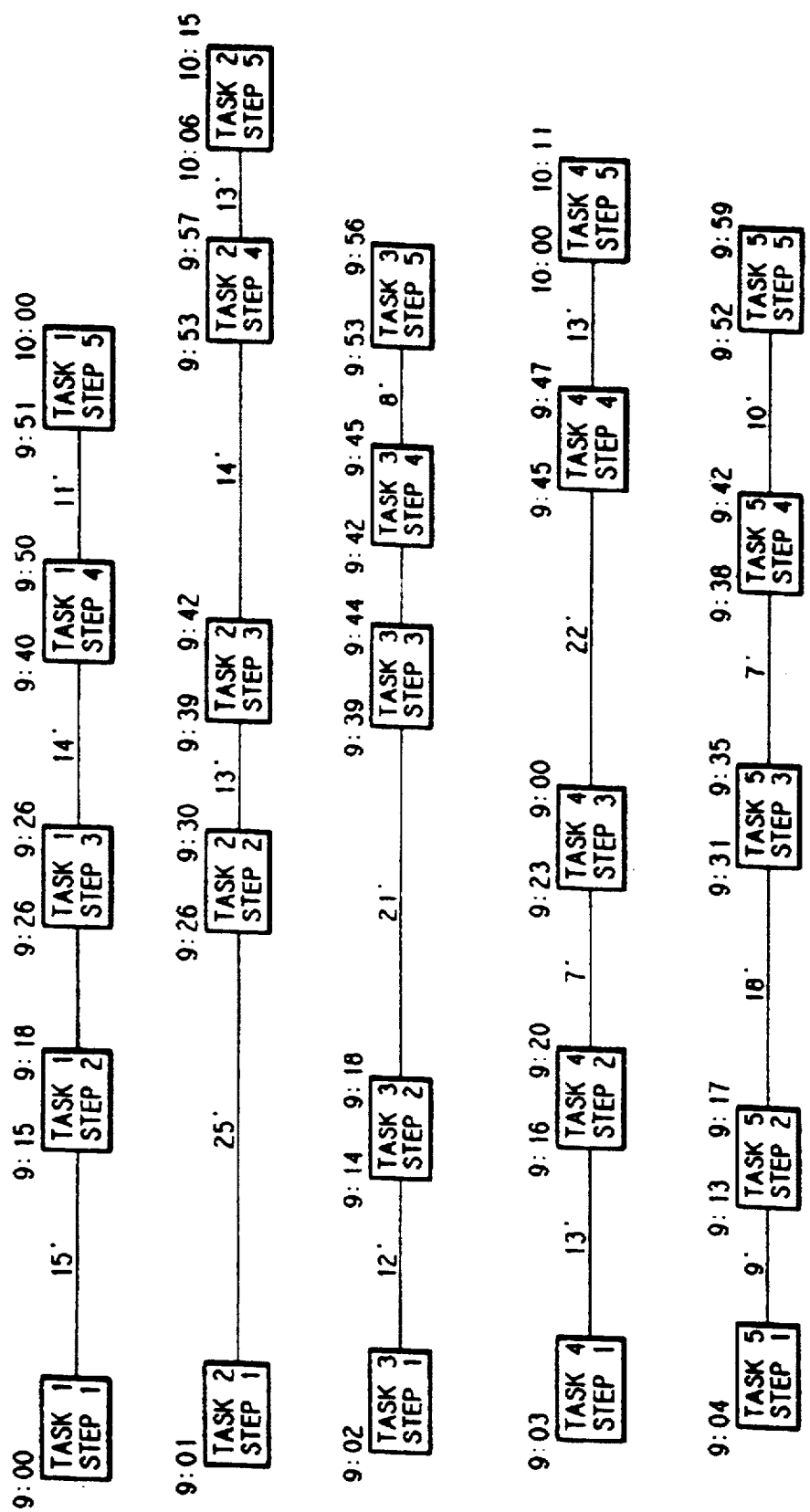
Figure 5:
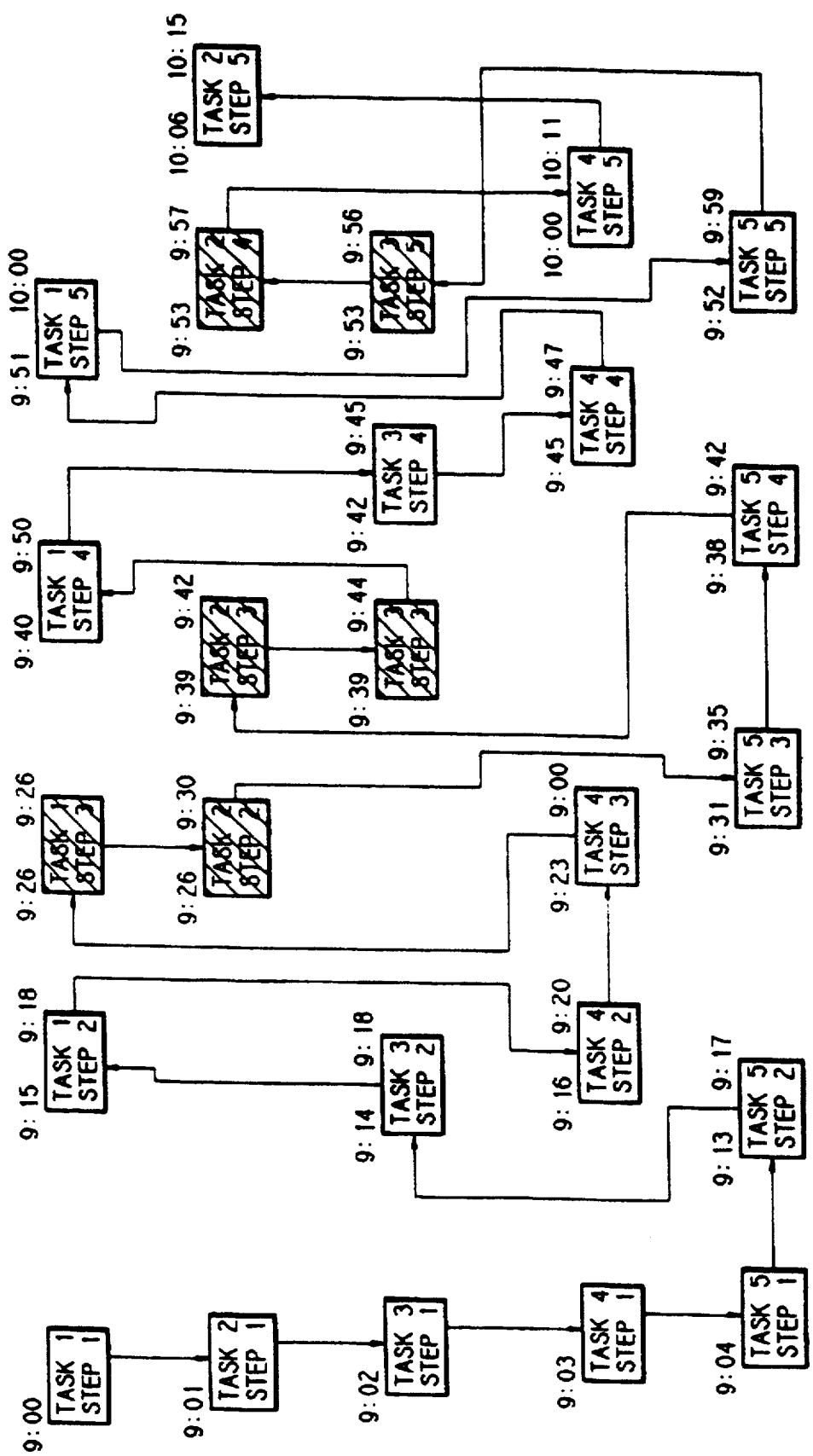

FIGS. 3D-1 and 3D-2 show a workstation having an incubation oven and a carrying medium for inserting slides 540 or slide pairs 543.

In a preferred embodiment, an incubation oven 620 comprises a chassis 621, an incubation chamber 622 a set of heat exchanger fins 623, a hydration fluid supply 624, an internal cooling element 625, a fill/drain control 626, a fluid waste receiver 627, a receiving element 628 for a carrying medium 630, and a set of heat fins 629.

The incubation chamber 622 is supported by the chassis 621 and comprises a set of chamber walls 631 disposed in a generally rectilinear form 632 with a set of rounded corners 633 to form a first part of a sealed fluid-tight box 634 when the carrying medium 630 is disposed for operation. When the carrying medium 630 is disposed for operation, the slides 540 or slide pairs 543 in the carrying medium 630 may be heated with moist heat formed by heating the incubation chamber 622 while disposing a hydrating fluid therein, and thus incubated. Incubation of slides 540 or slide pairs 543 is known in the art.

The heat exchanger fins 623 are disposed in the incubation chamber 622 in an array. The array is disposed to match, but not contact, a set of slides 540 or slide pairs 543 disposed in the carrying medium 630. There should be one of the heat exchanger fins 623 for each slide 540 or slide pair 543, or at the least, for each pair of slides 540 or slide pairs 543. Each one of the heat exchanger fins 623 has a height sufficient to heat the entire slide 540 or slide pair 543, or at least a portion of the slide 540 or slide pair 543 to include the sample.

A horizontal plate isolates the heat exchanger fins 623 from the hydration fluid supply 624. The heat exchanger fins 623 may each comprise a resistive element such as a metallic wire, coupled to a voltage source 634 disposed outside the incubation chamber 622. The voltage source 634 is coupled to a voltage regulator 635 to regulate the temperature of the incubation chamber 622, and thus of the slides 540 or slide pairs 543, to a selected temperature in steps of 1 degree Celsius between ambient temperature to about 100 degrees Celsius. Heating elements and regulators are known in the art.

The incubation oven 620 is triggered when first coupled to the robotic system, and controlled to a temperature selected by the control station 14. Typically, the control station 14 will set the regulated temperature of the incubation oven 620 to a room temperature such as 25 degrees Celsius, will set the regulated temperature of the incubation oven 620 to an operating temperature such as 95 degrees Celsius a few minutes before the incubation oven 620 is to be used in a process step, and will set the regulated temperature of the incubation oven 620 to a room temperature or to a second operating temperature such as 37 degrees Celsius after the incubation oven 620 is used in a process step and before it is to be used in a second process step. Each process step designating the incubation oven 620 indicates an operating temperature for that process step.

The hydration fluid supply 624 comprises a source, such as a bottle, into which a hydrating fluid 636 is placed and from which hydrating fluid 636 is drawn during operation of the incubation oven 620, and a fluid well 637 in which a selected level of hydrating fluid 636 is maintained. The selected level of hydrating fluid 636 is maintained by means of an automatic replenisher having a combination of a reservoir and valve, disposed to maintain a constant level of hydrating fluid 636 in the fluid well 637 available for evaporation into the incubation chamber 622, similar to a bird feeder. The fill/drain control 626 provides for filling and draining the hydrating fluid 636 from the fluid well 637. Flow regulation and fluid level regulation are known in the art.

The selected level of hydrating fluid 636 may be adjusted to account for differing assay protocols. For example, an assay protocol for hybridization may generally require heating and cooling without drying out the sample. Alternatively, other assay protocols, such as those for heating a xylene mixture, may require a relatively dry heat.

In a preferred embodiment, the hydrating fluid 636 may comprise (per 10 liters) 9980 milliliters nanopure water, 20 milliliters Tween-20, and 10 grams sorbic acid. However, those skilled in the art would recognize, after perusal of this application that plain water, a known buffer solution, or another substance for incubation of tissue, would also be workable for the hydrating fluid 636, and that such substances would be within the scope and spirit of the invention.

The internal cooling element 625 is disposed in the chassis 621 near the incubation chamber 622 to cool the incubation oven 620 and those of its elements that do not need to have an raised temperature. The internal cooling element 625 comprises a fan 638 coupled to the voltage source 634 and to a temperature regulator 639, such as a thermostat, to maintain the chassis 621 at a selected temperature. The heat fins 629 also serve to aid in regulating the incubation chamber 622 to a selected temperature. Temperature regulation is known in the art.

The fluid waste receiver 627 comprises a chamber for receiving excess hydrating fluid 636 not evaporated by the heat exchanger fins 623, and other fluids that may be condensed by the internal cooling element 625. The fluid waste receiver 627 may be detachable for emptying.

The receiving element 628 comprises a set of receiving slots 640 molded into a bottom 641 of the incubation chamber 622, disposed to receive a set of feet 641 of the carrying medium 630. The carrying medium's feet 641 are similar to those of the first standardized slide carrier 560 or the second standardized slide carrier 600, so the receiving element 628 is similar to the top indentations 310 of the tile 301.

The carrying medium 630 for inserting slides 540 or slide pairs 543 into the incubation oven 620 is similar to the first standardized slide carrier 560, and comprises a frame 651, a coupling ring 652, a set of slide frames 653, and a set of feet 654. It further comprises a slide holder cover 655, a set of ventilation openings 656, and a cover latch 657.

The frame 651 is similar to the first standardized slide carrier's frame 561, and comprises a metal frame comprising a set of four horizontal elements (a top 658, a slide top 659, a slide bottom 660, and a bottom 661), and a set of four support posts 662. Rather than being flat as in the first standardized slide carrier's frame 561, the bottom 661 comprises a V shape with the bottom of the V shape in the center, to carry condensation away from the slides 540 or slide pairs 543. Other frame elements may also be bent at angles or into V shapes to direct condensation away from the slides 540 or slide pairs 543.

The slide holder cover 655 is disposed over the frame 651, and comprises a solid shell of a lightweight material such as a rigid plastic. The slide holder cover 655 comprises a set of four shell sides 662, a set of downward sloping corners 663, and a rounded topmost part 664, with the set of ventilation openings 656 defined by gaps in the topmost part 664.

The ventilation openings 656 comprise a set of openings 665 with a slidable disk 666 disposed around the coupling ring 652 (and related assembly) similar to the first standardized slide carrier's coupling ring 562 (and related assembly, such as the ring base 571, ring bumper 573, plastic disk 574, circular hole 575, circular hole 576, circular raised lip 577, and circular flat portion 578). The slidable disk 666 defines a set of slidable openings 667 generally corresponding to the ventilation openings 656, a set of slidable masks 668 also generally corresponding to the ventilation openings 656, and a lip 669 for sliding the slidable disk 666 to adjust the ventilation openings 656 by alternatively uncovering them with the slidable openings 667 or covering them with the slidable masks 668.

The slide holder cover 655 and the ventilation openings 656 are preferably shaped (as shown in FIG. 3D) to optimize effects of condensation of the hydrating fluid 636 and carry condensate away from the slides 540 or slide pairs 543. In particular, the slide holder cover 655 and the ventilation openings 656 are preferably trapezoidally shaped to cause the hydrating fluid 636 to condense and drip back into the incubating chamber 622, rather than evaporate into the local atmosphere.

The cover latch 657 comprises a V-shaped element 669 coupled to one of the shell sides 662, and a peg 670 coupled to the slide top 659. The V-shaped element 669 is disposed to just fit over the peg 670, so that a reasonably firm, but still easily removable, latch is made.

In a preferred embodiment, the incubation oven 620 is prepared with the following steps:

1. The operator fills the hydration fluid supply 624 and, if necessary, empties the fluid waste receiver 627.
2. The operator adjusts the fill/drain control 626 to regulate the level of hydrating fluid 636 to a selected level.
3. The operator prepares the slides 540 or slide pairs 543 according to a desired assay protocol, and configures the robotic system to perform the program for that assay protocol.
4. The operator inserts the slides 540 or slide pairs 543 into the carrying medium 630 by means of the slide holder cover 655, and replaces the slide holder cover 655 on the carrying medium 630. The operator sets the ventilation openings 656 to adjust for ambient humidity levels. Preferably, the ventilation openings 656 should be as wide open as possible while at the same time allowing the chemistry in the capillary gap of the slide pair 543 to maintain a level above 75% of capillary gap for an entire hybridization process step.
5. The operator places the slide carrying medium 630 in a HOME position tile 301 and directs the control station 14 to initiate the assay protocol.

The incubation oven 620 may be used in conjunction with inventions disclosed in one or more of the following U.S. Patents, hereby incorporated by reference as if fully set forth herein: U.S. Pat. Nos. 4,731,335; 4,777,020; 4,798,706; 4,801,431; 4,975,250; 5,002,736; 5,023,187; and 5,116,727.

In a preferred embodiment, where the workstation 13 comprises a device that should be engaged to operate on the sample, coupling the carrying medium to the device requires two steps: (1) The carrying medium is first coupled to or inserted into the device. (2) The device is triggered.

As with the incubation oven 620, the device may be triggered when first coupled to the system, and controlled by the control station 14. Alternatively, the device may be triggered by a switch (triggered by contact with the robotic arm), or preferably, by contact with the carrying medium by means of a contact switch, proximity switch, or a weight-triggered switch that detects the presence of the carrying medium or its having been coupled to the device.

Operation of the Package in the Robotic System

FIG. 3E is a flowchart of a preferred method of operating the robotic system with standardized packages and contents.

In a preferred embodiment, at a step 681, the tray 406 is filled with contents 542 comprising a selected amount of a selected reagent, other bioactive or chemoactive compound or mixture, or buffer.

At a step 682, the tray 406 has the cover 407 sealed thereon.

At a step 683, the tray 406, contents 542, and cover 407, are transported to a location having the robotic device 10. The configuration of the well dividers 522 permits the liquid contents to flow easily between the inside wells 521 during shipment and prior to placement in a tile 301.

In a preferred embodiment, the contents 542 of the tray 406 comprise one of a set of standardized selected reagents, other bioactive or chemoactive compounds or mixtures, or buffers, known to programmers of the robotic device 10. Because the contents 542 are standardized and known to programmers of the robotic device 10, an assay protocol may be preprogrammed and preloaded into the robotic device 10, for dynamic selection by an operator.

At a step 684, an operator of the robotic device 10 places a plurality of tiles 301 in the robotic device 10, and affixes those tiles 301 to the robotic device 10 with screws or other affixing objects.

At a step 685, the operator places one or more trays 406, each with its cover 407 still sealed, in a set of selected tiles 301.

At a step 686, the operator removes the covers 407 from the trays 406, instructs the robotic device 10 as to the location of each such tray 406 and its contents 542, and commands the robotic device 10 to begin one or more preprogrammed assay protocols. As described herein, the preprogrammed assay protocols may be one or more assay protocols with which the robotic device 10 is started, or may be one or more assay protocols that are added to an already ongoing set of assay protocols.

In a preferred embodiment, the strength of the fixative that affixes the cover 407 to the tray 406 exceeds any likely force for removal that might occur during shipment, but is less than a force for removal required for overcoming the spring lock 405. The operator may therefore remove the cover 407 from the tray 406 while the tray 406 is locked into the tile 301 by means of the lever 404 and the spring lock 405, without the tray 406 coming undone from the tile 301 due to the force of removal.

In a preferred embodiment, the robotic device 10 comprises a memory with a set of preprogrammed assay protocols, that have been previously programmed and loaded into memory, and that are selectable by a set of assay protocol names. The operator may therefore select an assay protocol by name at the time it is desired to conduct the assay, without having to reprogram the robotic device 10 each time it is desired to conduct that assay. In a preferred embodiment, a set of preprogrammed assay protocols are previously programmed, transferred to an intermediate storage medium such as a diskette, tape, or network, and loaded into the memory of the robotic device 10 by means of a operator command. The operator command to load the preprogrammed protocol may also be subject to security confirmation.

The standardized contents 542 of the trays 406 may comprise a set of alcohols.

The standardized contents 542 of the trays 406 may comprise a set of antibodies.

The standardized contents 542 of the trays 406 may comprise a set of blocking agents, such as hydrogen peroxide block or a serum block.

The standardized contents 542 of the trays 406 may comprise a set of buffer solutions, preferably a phosphate buffered saline with a pH of about 7.2. In a preferred embodiment, buffer solutions should include a surfactant for best operation with the capillary gap of the slide pair 542. The surfactant is bridge or preferably tween (the latter available from Fisher Scientific Co.), optimized for use with the capillary gap in a slide pair 543 with about a 1% to 2% solution of tween in water.

The standardized contents 542 of the trays 406 may comprise a set of chromagens, including those that relate to the visible range or another range of the electromagnetic spectrum (such as infrared or ultraviolet).

The standardized contents 542 of the trays 406 may comprise a set of DNA probes.

The standardized contents 542 of the trays 406 may comprise a set of enzymes.

The standardized contents 542 of the trays 406 may comprise a set of fixatives.

The standardized contents 542 of the trays 406 may comprise a set of linking molecules, such as avidin biotin conjugate.

The standardized contents 542 of the trays 406 may comprise a set of staining agents, such as hematoxylin stain or eosin stain.

The standardized contents 542 of the trays 406 may comprise a set of washes, such as water.

A set of preferred assay protocols is described in an appendix.

System Control by Operator

In order to use the system of this invention the operator (which might be a human user or a control processor) may first determine the processes that are to be carried out the apparatus. Each step of each process may be defined. To assist the user an index of work stations may be provided to allow the user to determine which process steps can be employed. Alternatively, each work station can be represented by an icon on the CRT display and a help index made available that the user may determine the capabilities of each work station by referring to the icon and its associated help screen.

As previously described with reference to FIGS. 1-2, the apparatus of the invention uses a locating grid or template presenting the operational work area reachable by the robotic device 10 in which the work station locations may be defined. Each position on the grid is accurately determined and can be imparted to the computer to provide certainty of location. The exact relative position of each work station may be stored in the control system. The use of the predetermined grid locations permits the user of this system to have the freedom of designing individual templates to match the user's need and to design the steps of a process to provide relative limited ability in creating processes, limited only by the available work stations.

Figure 6:
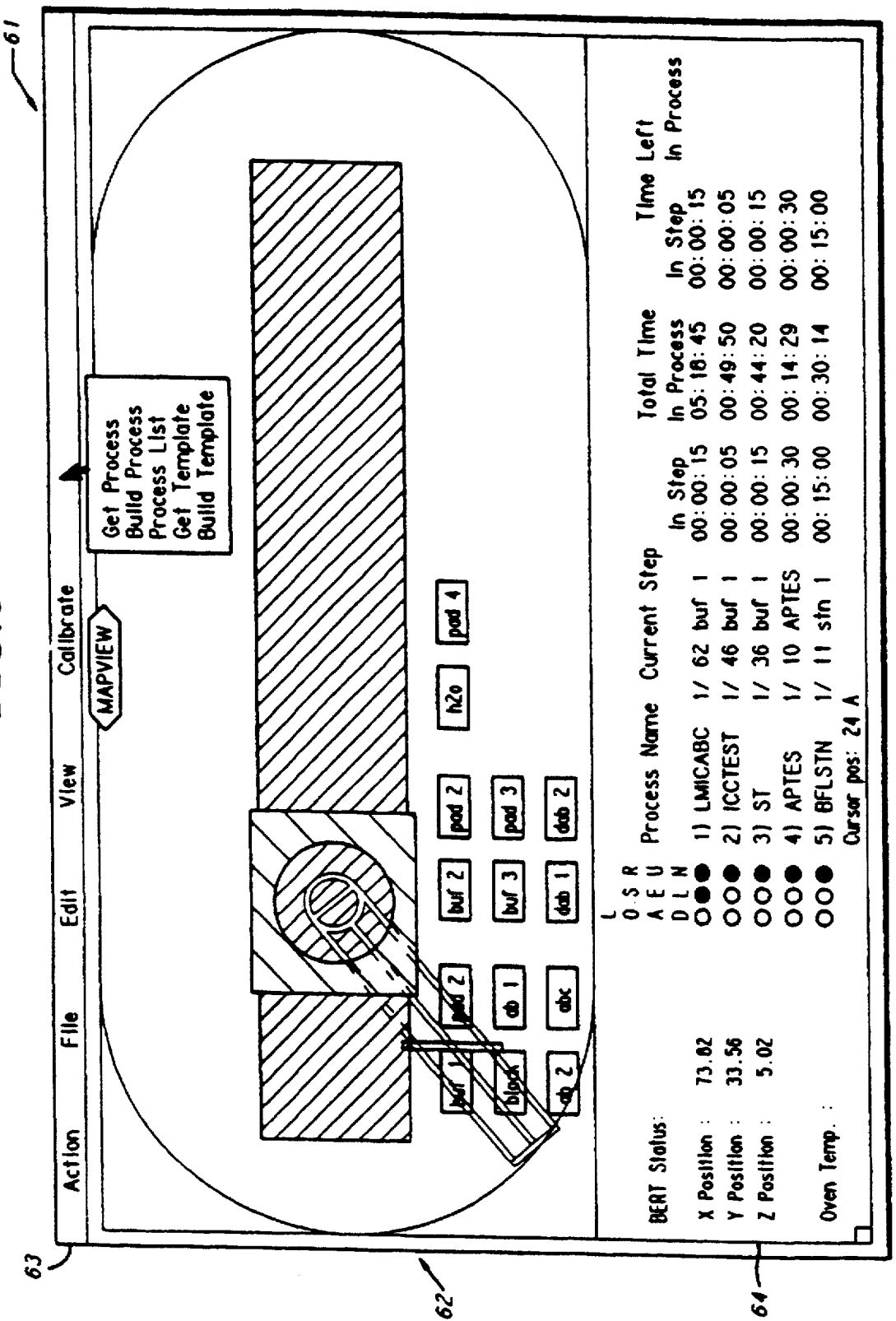
Figure 7:
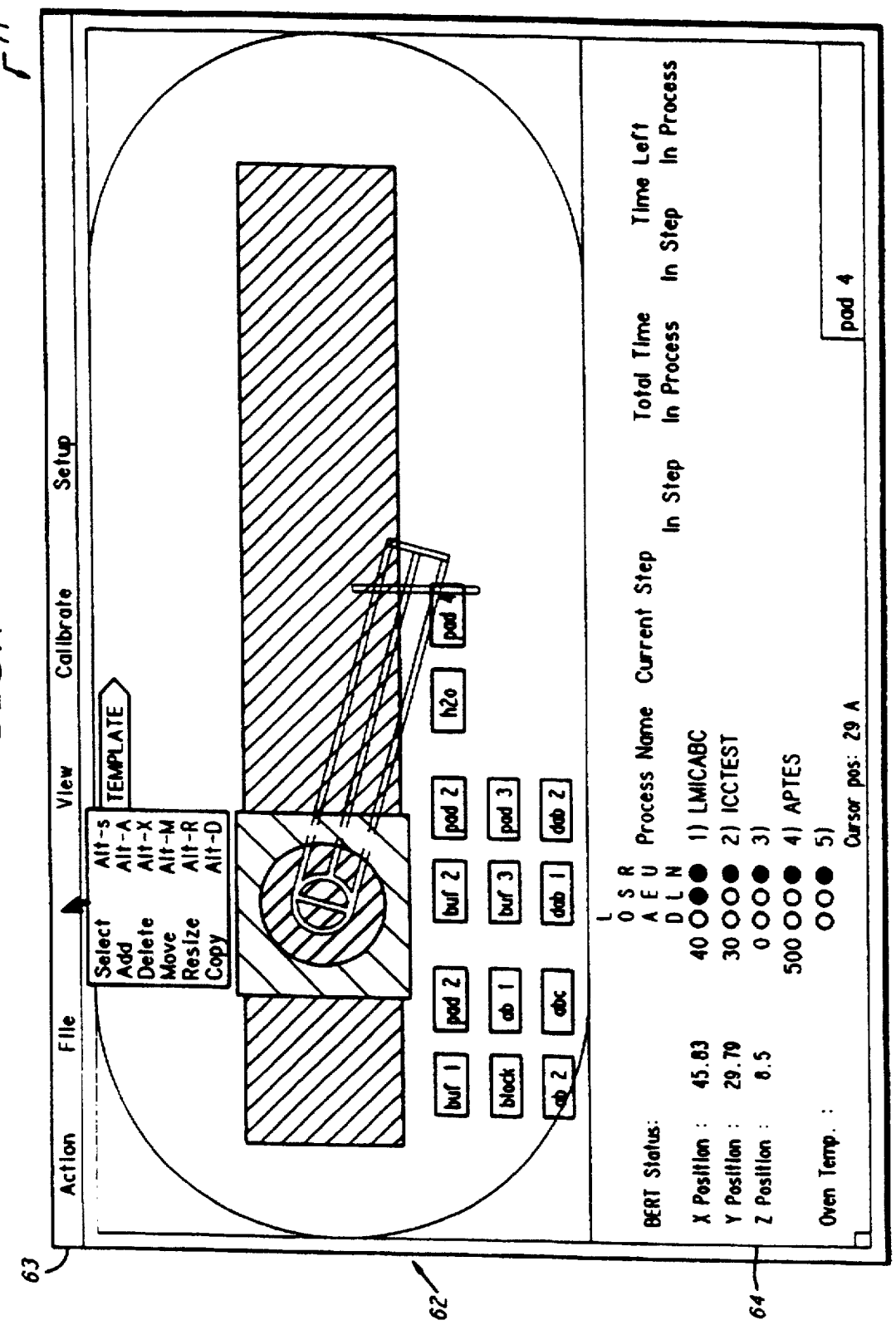
FIG. 7 shows a template building screen as viewed by an operator.
Figure 8:
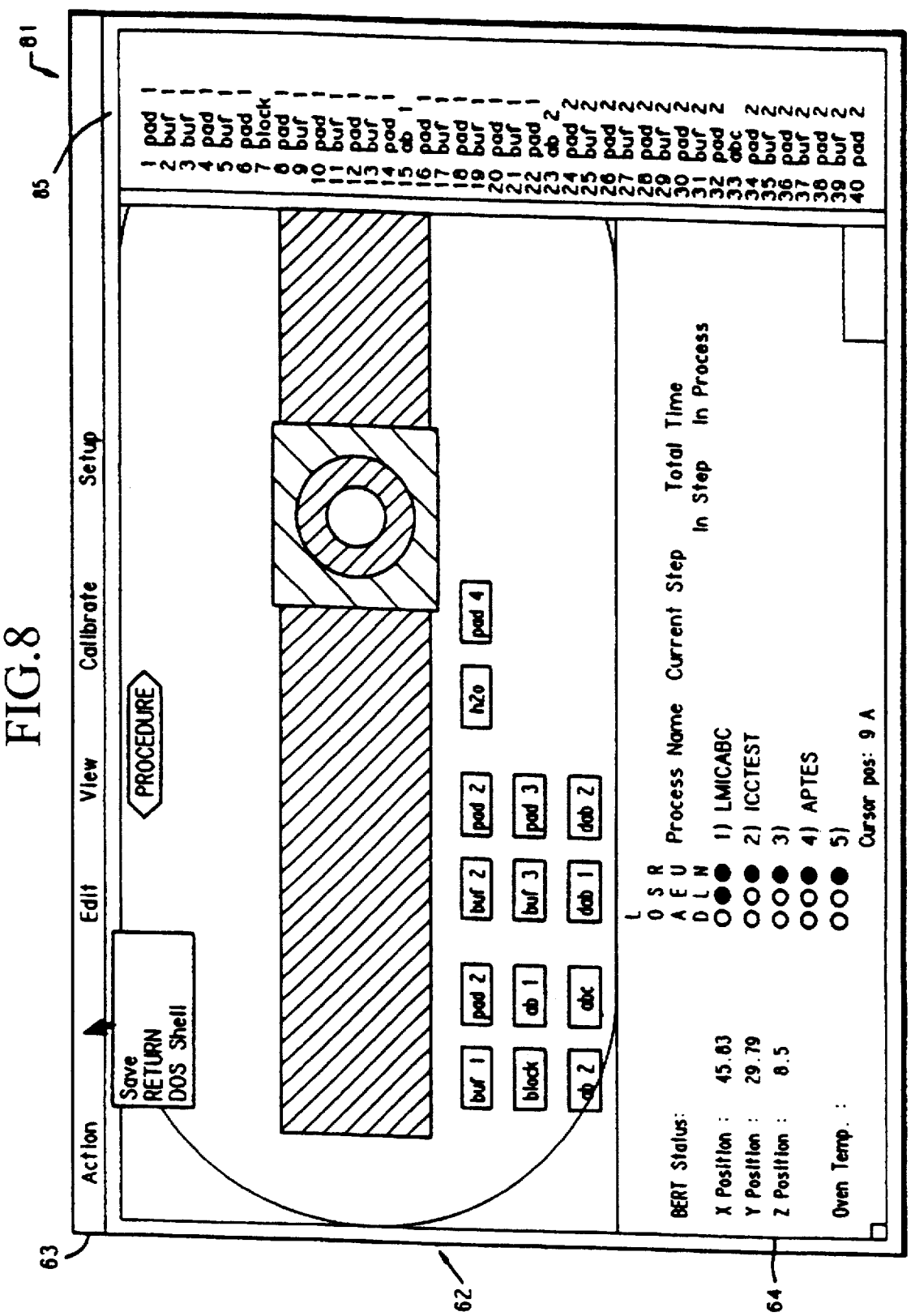
FIG. 8 shows a process building screen as viewed by an operator.

A graphic replica of the grid in which the work stations located is provided on the screen of the computer, such as shown in FIGS. 6-8. Included in this graphic is the robotic arm position. In order to quickly input the steps of a process to the computer (1) a template builder and (2) a process builder have been created to interact with graphic replica of the work area. These two tools, template builder and process builder, allow the user to design a new process or modify an old process, easily and quickly without the need to have knowledge of computer programming. Through the use of a keyboard or mouse, the two builder tools are rendered interactive with the user.

A work station grid area may have holes disposed on one inch centers, or any other predetermined pattern. The columns of holes may be identified by letters while the rows of locating holes may be identified by numbers. Thus each hole can be uniquely identified by a letter-number combination.

Work station units or peripherals have been designed which have elements which cooperate with the grid locating holes and thus facilitate the exact location of each station. When located on the grid each work station will have a unique describer positively identifying its location.

Thus the user may commence operating the system by viewing a graphic representation of the work area surrounded by icons representing various work stations. As will be described below the user can quickly design a new template if so desired. Alternatively, the template may be called up from a disk by the computer.

The steps of the process are communicated to the computer through the use of an interactive peripheral such as a mouse. The operator locates the mouse cursor on the icon representing the first step of the process and drags the icon to the desired location. Thus by pointing and clicking the mouse the work stations necessary to accomplish the steps of the process are disposed on the graphic grid. It is of course desirable that the physical workstations be located on the grid in the locations shown on the display. Alternatively, the location of the work station can be fed into the computer in other ways, such as through the keyboard or even by locating the physical work station on the grid with feedback to the computer identifying the work station and location.

Thus an unsophisticated user has the ability to design processes quickly imparting great flexibility to this apparatus. It should of course be recognized that this information can be stored on a disk and the apparatus set up accomplished by reading the information off a disk into the memory of the computer.

In creating the template the operator uses a mouse to draw replicas of each station on the screen, such as shown in FIG. 7, a template building screen. Each station is given a unique identification which may be a name, symbol or code. The dimensions of the station may be drawn on the screen and in particular it is essential that the height of the work station is recorded. The position, identification, height and other dimensional criteria are stored in the RAM memory of the computer CPU. When the template is completed it may be stored to disk as a template file, to be recalled as needed.

As is not unusual in the operation of computers, provisions are made to add, delete, move, resize or duplicate any of the stations. Any available template previously stored may be recalled to be used or to assist in the creation of new templates. Of course the apparatus may have the ability to enable the operator to print out a graphic replica of the screen and a list of station positions, identifications, heights or other dimensions.

Once the template is complete the operator may use the stations of the template to create a process, step by step.

The process builder, like the template builder, uses a graphic replica of the workstation area on the computer screen, such as shown in FIG. 8, a process building screen. One of the templates previously created by the template tool builder described above, is recalled from memory and displayed on the screen together with the work area. The screen cursor is moved to the desired station icon and the particular station is selected. This procedure may utilize a mouse and a point and click procedure.

Each station of the process is selected in sequence and the station is then added to a list denoting the steps of the process in sequential order. The robotic device would ultimately be controlled to move to each of these stations in the order in which they were added the process list. Since the characteristics of each work station were previously stored in the computer, the robotic device would be programmed for the proper movement. For example, the height of each station was previously stored in the memory, and if the robotic arm were to traverse the area in which a high work station was located, it would be instructed to elevate the hand so that any sample mounted thereon would clear the high work station. It is also possible to design the operational area to have clear paths or lanes defining travel routes for the robotic device 10. In any event, the movement of the robotic device among the workstations may be designed to be free of collisions based upon recognition of the entity, position and geometry of the work stations. As will appreciated as the number of work stations increase the amount of information that should be considered in order to avoid collisions and otherwise avoid conflicts in instructions also increases.

Figure 9:
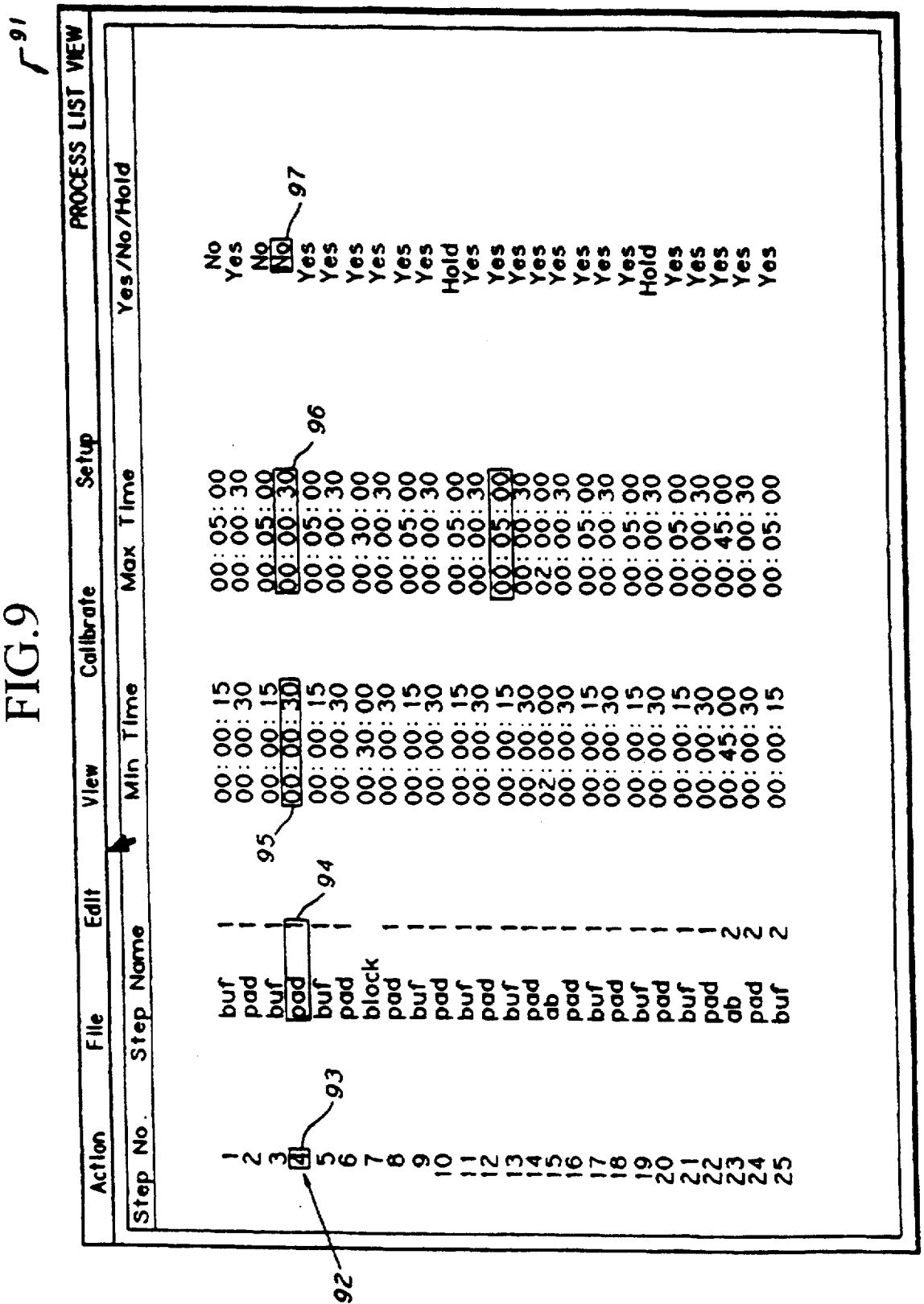
FIG. 9 shows a process timing screen as viewed by an operator.

Following the graphic design of the steps of the process, the process list would be called up on the screen and the procedure for each step would be imparted, such as shown in FIG. 9. This procedure would essentially indicate a range of time each sample should remain at each station. For each step a minimum time and a maximum time for the sample to remain at the work station would be recorded. As noted herein, the minimum time may be specified to be zero, and the maximum time may be specified to be infinity. The times for each station, except where the timing is critical, would allow the system a timing window which can be used to avoid timing conflicts between different steps of separate tasks and thus maximize the multitasking capabilities of the apparatus.

Pseudocode for Designing or Running New Processes

The method carried out by the control station 14 for template building and process building may be described by pseudocode shown in Tables 2-3 herein, respectively. It would be clear to one of ordinary skill in the art, after perusal of the specification, drawings and claims herein, that modification of known processor systems to perform the functions disclosed in this pseudocode (as well as in other pseudocode disclosed herein) would be a straightforward task and would not require undue experimentation.

TABLE 2

Template Builder

```
procedure template_tool();
set up screen;
draw robot replica graphic;
draw grid;
display mouse cursor;
select template design tool;
while (not finished)
    select tool;
    case (edit tool)
        add:        draw new station on screen via mouse by
                    dragging mouse away from start point while
                    having mouse button 1 depressed;
                    update screen with a rectangle being
                    displayed along cursor displacement;
                    enter id via keyboard;
                    position height of station;
                    store position and id;
        select:     move cursor to station via mouse;
                    click mouse to select;
                    selected station changes color to show it is
                    selected;
        delete:     click mouse button 1 to delete;
        move:       place move crosshair on selected station;
                    place cursor on crosshair;
                    press mouse button 1 down and drag station to
                    new position;
                    screen update after each new grid position
                    move;
        resize:     place resize crosshair on selected
                    station;
                    place cursor on crosshair;
                    press mouse button 1 down and drag station to
                    new size;
                    screen update after each new size;
        duplicate:  get current selected station position, size
                    and height information;
                    offset duplicate to new position;
                    add id;
                    store new station position and id;
```

TABLE 3

Process Builder

```
procedure process_tool();
set up screen;
draw robot replica graphic;
draw grid;
draw process list;
display mouse cursor;
    case (file tool)
        get template:   display list of template files;
                        select via mouse cursor;
                        open selected template;
                        display template stations on screen;
                        hold station record in RAM;
        get process:    display list of process files;
                        select via mouse cursor;
                        open selected process;
                        display process list in list window;
                        display associate template stations on
                        the screen;
                        hold process station records in RAM;
        save process:   display list of process files;
                        select via cursor or enter new name via
                        keyboard;
                        store process file to disk;
    case (file tool) end;
    case (select_tool):
        if cursor in work station area and on a station and mouse
        button 1 down then add station to process list;
```

TABLE 3-continued

Process Builder

```
        if cursor in process list and on list member and mouse
            button 1 down the delete from list;
        case (select_tool) end;
    case (window select)
        Process List:        (1) set up screen;
                             (2) display process in list mode;
                             (3) enter min/max time via keyboard;
                             (4) scroll down screen;
                             (5) do steps 3-4 until finished;
                             (6) exit back to previous window;
        Run/Control:         return to Run/Control window;
end (process tool);
```

After the station sequence has been entered and the times for each step recorded, the process may be stored to disk as a process file. The process file may be loaded in the future and the apparatus used to run the same process at a later date. Of course the template file may be linked to the process file so that when a process is called up from storage and run on the computer the template files used in the process may be automatically called up and displayed on the computer screen.

The procedure list on which the times at each step were recorded may be called up at any time and for the stations still not used by the robotic device, adjustments to the timing could be made provided that the steps in the process which are to have their timing altered have not been reached. Thus the operator can adjust the timing of the steps even as the process is running.

Visual Operator Interface

FIG. 6 shows a multitask monitoring screen 61 as viewed by an operator. A multitask monitoring screen 61 may be shown on a display device coupled to the computer 15, such as a display monitor. The multitask monitoring screen 61 may comprise a display section 62, a menu section 63, and a status section 64.

The display section 62 may show a representation of the robotic device 10, bench top 11, holes 12, work modules 13, and related equipment. For example, the display section 62 may show positions for workstations 13 for a selected process.

The menu section 63 may show command options and suboptions which are available to the operator and may allow the operator to select one or more command options and suboptions. For example, the menu section 63 may have a menu with the command options "GET PROCESS", "BUILD PROCESS", "PROCESS LIST", "GET TEMPLATE" and "BUILD TEMPLATE". The operator may display available command options and select one or more command options in the menu section 63, by means of a pointing device, such as a mouse, as is well known in the art.

The status section 64 may show a set of status information about processes. For example, the status section 64 may show five processes which are in progress, and may show for each process the current step it is on, the total time it has taken (both for the current step and for the entire process), and the time remaining that it will take (both for the current step and for the entire process). Note that elapsed time for the current step may be zero because the robotic device 11 might wait for the proper time before depositing the sample in the workstation 13 for that process step, e.g., holding the sample in the robotic hand 23 if travel from a prior step took less time than expected. The status section 64 may also show the X, Y and Z position of the robotic arm.

FIG. 7 shows a template building screen 71 as viewed by an operator. A template building screen 71 may be shown on a display device coupled to the computer 15, such as a display monitor, in like manner as the multitask monitoring screen 61. The template building screen 71 may comprise a display section 62, a menu section 63, and a status section 64, in like manner as the multitask monitoring screen 61.

When using the template building tool, described herein, the operator may view the template building screen 71 and manipulate the commands and elements thereon by means of a pointing device, such as a mouse. A detailed description of how the operator may use the template builder tool is given herein.

FIG. 8 shows a process building screen 81 as viewed by an operator. A process building screen 81 may be shown on a display device coupled to the computer 15, such as a display monitor, in like manner as the multitask monitoring screen 61. The process building screen 71 may comprise a display section 62, a menu section 63, and a status section 64, in like manner as the multitask monitoring screen 61, and a workstation section 85.

The workstation section 85 may show a set of names or other identifiers of workstations 13. The operator may select one or more workstations 13 for inclusion in a process, by means of a pointing device, such as a mouse.

When using the process building tool, described herein, the operator may view the process building screen 81 and manipulate the commands and elements thereon by means of a pointing device, such as a mouse. A detailed description of how the operator may use the process builder tool is given herein.

FIG. 9 shows a process timing screen 91 as viewed by an operator. A process timing screen 91 may be shown on a display device coupled to the computer 15, such as a display monitor, in like manner as the multitask monitoring screen 61. The process timing screen 91 may comprise a plurality of lines 92, each of which may have an identifier section 93, a name/descriptor section 94, a minimum time section 95 and a maximum time section 96.

When using the process building tool, described herein, the operator may view the process timing screen 91 and enter minimum times (in the minimum time section 95) and maximum times (in the maximum time section 96) for each process step at each line 92. Each process step may thus have a line 92 with an identifier in the identifier section 93 and a name or descriptor in the name/descriptor section 94.

The minimum time section 95 for a line 92 may specify a minimum time which the designated process step may take, which might be zero. If the minimum time is zero, additional data may be noted to indicate whether the designated process step may take a single tick of a timing clock for the robotic device 10, or if the designated process step may be skipped entirely.

The maximum time section 96 for a line 92 may specify a maximum time which the designated process step may take, which might be infinity. If the maximum time is infinity, the system may delay completion of the designated process step until after all other process steps with finite maximum time have been completed.

Each line 92 may also have an additional data section 97 for the designated process step, which may specify whether (1) the step is to be done, (2) the step is to be skipped, or (3) the process is to be "held" or temporarily halted at the designated process step for input from the operator. In the latter case, for example, the process might be "held" at the designated process step until an operator confirms that the process should continue.

Multitasking and Optimization

Having delineated all the steps of all the procedures, the computer may determine the most efficient manner for carrying out the procedure. The task would be simple if the steps of the first process were to be completed before the apparatus started on the second process. Through the use of time interleaving, multiplexing or multitasking the computer is utilized to keep track of multiple operations so as to perform a number of different processes each having a multiplicity of steps simultaneously.

In multitasking, a number of samples, each undergoing separate exposures may all be worked on simultaneously. In time interleaving, the robotic arm may operate through a sequence which is determined by the timing of the individual steps of many processes and the robotic arm transports different samples in a time efficient sequence rather than a process ordered sequence. Although the robotic device can only move one sample to a work station at a time, the entire system is continuously monitoring, scheduling and processing all tasks and their times at each station concurrently. At each step the process performed at that workstation continues (e.g., chemical reactions) even when the robotic arm is not currently attending to it. In other words, the sample is disposed in the workstation and the robotic arm continues to grasp another sample. The process step continues to work on the first sample while the robotic arm is attending or transporting the second sample. The multiple process steps that are being done, one to each sample, are being done in parallel and are not serial processes.

In fact the robotic arm works on a sample for a short period of time during which it usually transports a sample to a work station and then leaves that sample and works on another sample or samples before returning again to the first sample. Thus the robotic device work on each sample is suspended during the time interval that it is working on another sample or during which the samples are being processed at a work station.

The multitasking of the different processes is dependent upon the instructions issued to the robotic device, relative to the timing of each of the steps in the multiple processes and the optimization of the multitasking operations, to move the samples at the scheduled times determined by the computer inputs.

The computer control (software) may first determine all the robotic movements necessary to complete the entire run of all the steps in all the processes to be run. This determination may be completed before any movement is initiated. If at any time during the running of the multitasking any steps are added to one or more of the processes or any of the steps are reconfigured during the run, a new determination may be completed wherein the computer recalculates all the movements necessary to complete the run and insures that there is no time interference created by the modification to the run. This method of predetermining the movements can of course be replaced by a real time method of determining movement but it is believed that the predetermining method is more advantageous. The predetermining method identifies time conflicts, if any, where the robotic device would be required to perform two tasks simultaneously, resolves any such conflicts that may exist, and optimizes the schedule for the minimum time required to complete the entire run of the multiple processes.

This method of predetermination employs certain decision making procedures which are designed to permit the computer to resolve time conflicts and iteratively optimize the schedule. An iterative optimization method is used because the complexity of scheduling different multiple tasks, each with the possibility of having multiple critically timed steps, is too complex to be solved by using mathematical techniques. In addition, the decision making rules allow the resolution of other conflicting requirements for other resources such as the peripheral equipment or work station modules, which may be used in conjunction with the robotic equipment.

As described above, a predetermined schedule may be developed to resolve time and resource conflicts and the schedule may be iteratively optimized to minimize the time required to complete the steps of the multiple processes. In order to interleave the steps of the multiple processes each step of each task is examined at predetermined intervals, e.g., one minute. A calculation is made of the time to completion of the current step. If the step incubation time is finished a move condition results. If that is the only move condition during this time, i.e., only one move condition occurs, the robotic device will be scheduled to move to the next step in accordance with the predetermined schedule. However, if more than one sample is scheduled to move time arbitration ensues. Time arbitration determines the fuzzy time window for each of the time conflicting steps and selects the sample in the most time critical step to move. If more than one step has a critical time, the computer compares the times during the previous movement and varies the timing of the previous tasks to resolve or prevent bottlenecks from occurring. In a similar manner a single resource can be scheduled to work on two different samples during the same time period and such conflicts can be resolved in a similar manner using the arbitration method.

Pseudocode for Multitasking

The method carried out by the control station 14 for multitasking may be described by pseudocode shown in Tables 4–8 herein. It would be clear to one of ordinary skill in the art, after perusal of the specification, drawings and claims herein, that modification of known processor systems to perform the functions disclosed in this pseudocode (as well as in other pseudocode disclosed herein) would be a straightforward task and would not require undue experimentation.

TABLE 4

Multitasking Data Structure

```
STRUCTURE TASK ARRAY [ 1500 elements ]
    BYTE       PROCESS NUMBER;
    BYTE       TASK NUMBER;
    CHAR [25]  TASK NAME;
    INTEGER    TASK X COORDINATE OF
               WORKSTATION;
    INTEGER    TASK Y COORDINATE OF
               WORKSTATION;
    LONG INTEGER ENCODED REAL TIME FOR
               PICKUP OR DROPOFF;
    CHAR [1]   DROPOFF/PICKUP FLAG;
    CHAR [5]   MOVE_FLAG;
                { When TRUE the process flagged needs to move to
                next task in progress. This information is entered into
                the task array. If multiple flags are set simultaneously
                the process steps must be arbitrated. }
    CHAR [5]   RESOURCE_FLAG;
                { If set TRUE, two or more tasks require the same
                resource. Resource arbitration is done to resolve all
                conflicts. }
```

TABLE 5

Multitasking (Build Schedule)

```
PROCEDURE BUILD_MULITTASK SCHEDULE ()
    { This routine is called a number of times with different
    seeding to build a statistical sampling of a number of
    schedules. The calling routine picks the most optimal schedule
    to run. }
BEGIN
    { Initialize timer and pick a process for first move. For
    iterative tasks, processes will be started in various orders to
    seed task builder and establish different scheduling. At each
    timer tick all processes are examined to check whether it is
    time to move to next position. If TRUE the task will be
    entered into the task array at the scheduled time. If more
    than one process needs movement at the same timer tick, time
    arbitration ensues. If two or more processes need the same
    resource, resource arbitration is undergone. This process
    continues until all tasks in all processes are complete. }
    TIMER = 0;
    START_FIRST_PROCESS;
    WHILE NOT ALL PROCESSES STARTED DO BEGIN
        INCREMENT TIMER BY 1;
        IF ANY TASK NEEDS MOVEMENT THEN
            SET TASK MOVE FLAG
            ELSE
            START_NEXT_PROCESS;
        IF MOVE_FLAG > 1 THEN
            TIME_ARBITRATE 0; {check for multiple moves }
        IF TASK_MOVE THEN ADD
            TASK TO TASK_ARRAY [TASK_COUNTER]
    END;
    WHILE NOT ALL PROCESSES COMPLETED DO BEGIN
        INCREMENT TIMER BY 1;
        IF ANY PROCESS NEEDS MOVEMENT THEN
        SET TASK MOVE FLAG;
        IF MOVE_FLAG > 1 THEN
            TIME_ARBITRATE 0; {check for multiple moves }
        IF TASK_MOVE THEN ADD
            TASK_ARRAY [TASK]; {check for resource use }
    END;
END;
```

TABLE 6

Multitasking (Time Arbitrate)

```
PROCEDURE TIME_ARBITRATE ()
    { If two or more processes must be moved simultaneously, the
    times are arbitrated, first by examining fuzzy time range and
    adjusting those process tasks with fuzzy time. If the
    colliding processes are critically timed the processes' prior
    tasks are rearranged to circumvent the collision. This
    procedure is called in REARRANGE_ARRAY (). }
    INTEGER FUZZY_TIME_{COMP = MAX_TIME; {set the
        compares to a maximum value }
    BYTE CRITICAL_FLAG     = 0; { initialize critical flag }
    BYTE CRITICAL_FLAG_ARRAY [5] = { 0, 0, 0, 0, 0 };
    BEGIN
        FOR I = 1 TO MAX_PROCESSES
            IF (PROCESS [I].MOVE_FLAG_SET AND
            FUZZY_TIME [I] < FUZZY_TIME_COMP)
            THEN BEGIN
                TASK MOVE = I;
                { finds shortest fuzzy time }
                FUZZY_TIME_COMP = FUZZY_TIME [I];
                IF (FUZZY_TIME = 0) THEN BEGIN
                    SET CRITICAL_FLAG;
                    SET CRITICAL_ARRAY [TASK];
                END;
            END;
        { If two or more processes need to move immediately a
        rearrangement of earlier interleaved tasks occurs to
        settle conflicts at this point if a fuzzy time range
        settle the conflict the process with the shortest fuzzy
        time value is set to move. }
```

TABLE 6-continued

Multitasking (Time Arbitrate)

```
        IF CRITICAL_FLAG > 1 THEN REARRANGE_ARRAY ();
        ELSE
            ADD TASK_ARRAY [TASK_MOVE];
    END;
```

TABLE 7

Multitasking (Resource Arbitrate)

```
PROCEDURE RESOURCE_ARBITRATE ()
    { If two or more processes need the same resource (physical
    location), fuzzy times for the processes in question are
    examined to evaluate whether the time slack can settle the
    conflict. If not, the processes prior tasks are rearranged to
    circumvent the collision. }
    BYTE CRITICAL_FLAG     = 0; { initialize critical flag }
    BYTE CRITICAL_FLAG_ARRAY [5] = { 0, 0, 0, 0, 0 };
BEGIN
    { Compare process task fuzzy time with other process actual
    task time. }
        COMPARE CRITICAL_PROCESS_1_FUZZY_TIME
        WITH CRITICAL_PROCESS_2_TASK_TIME;
            IF >TASK_MOVE = PROCESS_2;
            ELSE
        COMPARE CRITICAL_PROCESS_2_FUZZY_TIME
        WITH CRITICAL_PROCESS_1_TASK TIME;
            IF >TASK_MOVE = PROCESS_1;
        IF TASK_MOVE TRUE
            ADD TASK_ARRAY [TASK_MOVE];
        ELSE BEGIN
            SET CRITICAL_FLAG;
            SET CRITICAL_FLAG_ARRAY [TASK];
            REARRANGE_TASK_ARRAY ();
        END;
    END;
```

TABLE 8

Multitasking (Rearrange Tasks)

```
PROCEDURE REARRANGE_TASK_ARRAY ()
    { To prevent conflicts which cannot be arbitrated with fuzzy
    timing the processes in conflict are examined at their previous
    step(s) and timing adjusted in that task to remedy the conflict
    at the current task. After time adjustment of the critical
    process the task array is reset to the newly adjusted position
    and returns to the multitask builder and reworks the rest of
    the tasks in all processes. }
BEGIN
    { Find the last time the critical process was moved. }
    REPEAT
        POSITION = POSITION - 1;
        UNTIL TASK_ARRAY [POSITION] =
        CRITICAL_FLAG_ARRAY [TASK];
    { Adjust timer. }
        INCREMENT TASK [TASK_ARRAY
        [POSITION].MIN_TIME] BY X;
    { Reset position and time. }
        SET POSITION TO CURRENT TASK_ARRAY VALUE;
        SET TIMER TO CURRENT TASK_ARRAY VALUE;
        RETURN TO MULTITASK_BUILDER;
    END;
```

It would be clear to one of ordinary skill in the art, after perusal of the specification, drawings and claims herein, that there is a multitude of interleave paths that can be taken to achieve multitasking of a plurality of processes. Each path will in all probability have a different time to complete all of the steps of all of the processes. In view of this it will be appreciated that for optimum efficiency it is necessary to select the optimum path which will take the minimum time to complete. As a practical matter an iterative process can be used in which the interleave path is computed several times. Each time the interleave variables are iterated they are ordered and computed differently so that different results are obtained for each iteration. The number of iterations necessary to arrive at an optimized path can be computed statistically by taking the number of steps in each task and the number of tasks to be performed. Since run time of the paths calculated from the numerous iterations follow a normal distribution curve, the minimum number of iterations necessary to achieve a path that will be among the faster run times can be calculated.

One technique for computing an optimal interleave path may compute a set of interleave paths by iterating a selected number of times in response to the number of steps in each task and the number of tasks to be performed. The number of iterations may alternatively be selected to be a fixed number, such as 20 iterations, that may be altered in response to a command from an operator.

In a preferred embodiment, multiple tasks may be run with disjoint workstations, since it is possible that a reagent, or other chemoactive or bioactive compound or mixture, at a workstation will be contaminated by the sample tissue on the slide. However, where it is believed that contamination would be minimal, or at least that effects of such contamination would be minimal, it would alternatively be preferable to share resources such as standard buffers, washes, and pads. In this alternative embodiment, a source for a standard buffer or wash would be made available by means of an automatic replenisher having a combination of a reservoir and valve, disposed to maintain a constant level of liquid available for dipping a slide, similar to a bird feeder.

In an alternative embodiment, it may be preferable to design protocols for multiple simultaneous tasks to use a maximum set of common reagents or workstations. It would be preferable to design such protocols in two parts, part 1 and part 2, separated by a selected time, so that a set of resources used in part 1 of the protocol are not used in part 2 of the protocol. With this design, a resource arbitration technique may more easily distinguish when it is possible to start a second instantiation of the same protocol.

A preferred set of protocols are shown in this specification, hereby incorporated by reference as if fully set forth herein. These protocols are Copyright 1994 Biotek Solutions, Inc., and their inclusion in this patent application is not a waiver of copyright or any of the rights afforded by copyright.

Each protocol is intended for operation on the TechMate (TM) robotic controller (available from Biotek Solutions, Inc. of Santa Barbara, Calif.), and includes the following sections:

a protocol program name, a brief title, and an expanded title;

a summary of the running time;

a description of the principles of operation for the protocol;

a description of the nature of the specimen(s) the protocol is intended to operate upon;

a description of the nature of the preparation for the specimen(s) the protocol is intended to operate upon;

a description of the nature of the preparation for chemical reagents the protocol is intended to operate with;

a description of the procedure used in operation of the protocol;

a description of the expected results from operation of the protocol;

a description of references for further information about the principles of operation for the protocol;

an ordered listing of program steps; and a map template for operation of the protocol.

For each protocol, the ordered listing of program steps comprises five columns:

a sequence number, indicating a step number for the indicated program step;

a protocol operation name, indicating a protocol operation to be performed at the indicated step number;

a minimum time duration, indicating a minimum duration the indicated protocol operation may be performed, in hours, minutes, and seconds;

a maximum time duration, indicating a maximum duration the indicated protocol operation may be performed, in hours, minutes, and seconds; and an indicator of whether the step is actually performed, where "Y"=yes and "N"=no; or an oven temperature may be designated.

The protocol operation may comprise one of the following:

100% 100% ethanol

50% EtOH 50% ethanol

5N HCL 5 normal hydrochloric acid

AALC absolute alcohol

AB1 primary antibody—AB1A and AB1B also indicate a primary antibody

AB2 secondary antibody

ABC avidin biotin conjugate

AP alkaline phosphatase (enzyme detection)

BLECH bleach

BLOK blocking antibody, i.e., a bioactive agent that blocks secondary antibodies that are already present in the robotic system BUFxxx a phosphate buffer, as noted herein CHROM GEN a chromagen DAB diamino benzidine ENZ an enzyme, e.g., to help open up antigenic sites EOSIN eosin FK a fluorescent chromagen H2O water HEMA hematoxylin HI WASH a high stringency (high ionic concentration) wash, typically used for DNA probes HOME a "home" location for starting and/or stopping an assay protocol HP HP block, e.g., to block enzymes that are endogenous to the robotic system HYPO sodium thiosulfate, a reducing agent used to remove some mercury-based fixatives IO iodine IP an immunoserum, e.g., for enzyme detection LO WASH a low stringency (low ionic concentration) wash, typically used for DNA probes ME BL methylene blue stain PADxxx a blotter, preferably ½ inch thick PARK a location to wait until a next step PROBE a DNA probe SCHIF Schiff reagent for a Schiff reaction STN a stain XY xylene Those skilled in the art will recognize, after perusal of this application, that other and further protocol operations, reagents, chemoactive or bioactive compounds, buffers, or other substances would be workable with the devices and substances disclosed herein, and are within the scope and spirit of the invention.

Alternative Embodiments

While preferred embodiments are disclosed herein, many variations are possible which remain within the concept, scope, and spirit of the invention, and these variations would become clear to those skilled in the art after perusal of this application.

For example, it would become clear to those skilled in the art that the devices and techniques described herein would be applicable to other processes, subject to standardization and robotic operation, and that such application would be within the concept, scope, and spirit of the invention. Such processes could include those related to developing film and those related to manufacture or testing of electronic circuits, printed circuit boards, or semiconductor wafers.

For a second example, it would become clear to those skilled in the art that the devices and techniques described herein for use with liquid would generally be applicable to processes using other flowable substances, including colloids, gels, or powders, and that such application would be within the concept, scope, and spirit of the invention.

We claim:

1. In a system for performing a plurality of independent analysis procedures simultaneously, each said procedure having a sample and at least one process step for operating on that sample, a device for coupling a robotic hand to a slide holder, comprising a first horizontal element defining a first hole adapted to be coupled with said robotic hand;

a second horizontal element disposed above said first horizontal and adapted to limit said first horizontal element from motion in a vertical direction, a defining a second hole;

a third horizontal element disposed below said first horizontal element and adapted to limit said first horizontal element from motion in a vertical direction, and defining a third hole;

said second hole disposed with at least some exposed area that is not exposed by said first hole, and said third hole disposed with at least some exposed area that is not exposed by said first hole, whereby said first horizontal element is capable of moving in response to coupling by said robotic hand by passing said robotic hand through said second hole and interacting with said first hole.

2. A device as in claim 1, comprising a bumper disposed above said first horizontal element.

3. A device as in claim 1, comprising a guiding member coupled to said first horizontal element, whereby small misalignments by said robotic hand cause said first horizontal element to move in response to coupling by said robotic hand.

4. A device as in claim 3, wherein said guiding member comprises a lip surrounding at least a part of said first hole.

5. A device as in claim 1, comprising means for coupling said second horizontal element to a frame.

6. A device as in claim 1, comprising means for coupling said second horizontal element to said third horizontal element, whereby said second horizontal element and said third horizontal element define a space for disposing said first horizontal element.

7. A device as in claim 1, wherein at least one of said second and third holes is substantially elliptical.

8. A device as in claim 1, wherein said first hole is substantially elliptical.

9. A device as in claim 1, wherein said first horizontal element comprises a disk.

10. A device as in claim 1, wherein said first horizontal element is substantially thinner than at least one of said second horizontal element and said third horizontal element.

11. In a system for performing a plurality of independent analysis procedures simultaneously, each said procedure having a sample and at least one process step for operating on that sample, a device for coupling a robotic hand to a slide holder, comprising:

a first horizontal element defining a first hole adapted to be coupled with said robotic hand;

a second horizontal element disposed above said first horizontal and adapted to limit said first horizontal element from motion in a vertical direction, a defining a second hole;

a third horizontal element disposed below said first horizontal element and adapted to limit said first horizontal element from motion in a vertical direction, and defining a third hole;

said second hole disposed with at least some exposed area that is not exposed by said first hole, and said third hole disposed with at least some exposed are that is not exposed by said first hole, whereby said first horizontal element is free to move in the horizontal plane and able to move in a limited fashion in the vertical direction in response to coupling by said robotic hand by passing said robotic hand through said second hole and interacting with said first hole.

* * * * *